(12) United States Patent
Martz et al.

(10) Patent No.: US 7,988,693 B2
(45) Date of Patent: Aug. 2, 2011

(54) CHISELS AND PROCEDURE FOR INSERTION OF SPINAL IMPLANT IN A SPINAL DISC SPACE

(75) Inventors: Erik O. Martz, Savage, MN (US); David Chow, West Chester, PA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1563 days.

(21) Appl. No.: 10/520,794

(22) PCT Filed: Jul. 11, 2003

(86) PCT No.: PCT/US03/21967
§ 371 (c)(1),
(2), (4) Date: Jan. 10, 2005

(87) PCT Pub. No.: WO2004/008976
PCT Pub. Date: Jan. 29, 2004

(65) Prior Publication Data
US 2005/0251146 A1    Nov. 10, 2005

Related U.S. Application Data

(60) Provisional application No. 60/397,232, filed on Jul. 19, 2002.

(51) Int. Cl.
*A61B 17/00* (2006.01)
(52) U.S. Cl. ....................................................... 606/84
(58) Field of Classification Search ............. 606/79, 606/82–85, 167, 170, 176, 184, 185
See application file for complete search history.

(56) References Cited

U.S. PATENT DOCUMENTS
695,783 A    3/1902    Beam
(Continued)

FOREIGN PATENT DOCUMENTS
WO    WO 99/09914    3/1999
(Continued)

OTHER PUBLICATIONS
International search report, Oct. 21, 2003.
(Continued)

*Primary Examiner* — Anu Ramana

(57) ABSTRACT

A chisel with U.V-shaped, saw tooth or other shaped opposing blades is used to form channels in adjacent vertebrae. The chisel has a projection extending from at least one of the top and bottom surfaces to limit depth of penetration into the vertebrae. A guide member may be attached to the forward tip of the chisel to guide the chisel into the disc space to uniformly chisel both adjacent vertebrae simultaneously to form a channel in the vertebrae. The so formed channels serve as sa guide for a second chisel having no guide member. The second chisel, which may be a box chisel, is used to complete the channels to the desired depth to receive an associated implant, typically of cortical bone. Other embodiments are disclosed in which a two step box chisel has a retractable guide member for initially guiding the chisel as it forms partial channels in the vertebrae disc space. The guide member is then retracted and the channels formed to the desired depth. The chisels include guide member pins which serve to both limit the extension and retraction of the guide member and also to serve to limit the depth of penetration of the chisel, physically and visually. The guide member may be retracted with a rotatable knob and a threaded engaged rod or with an axially displaceable pin and rod assembly attached to the guide member. A procedure for using the chisels is also disclosed.

41 Claims, 12 Drawing Sheets

U.S. PATENT DOCUMENTS

| | | | |
|---|---|---|---|
| 740,937 A | 10/1903 | Smith | |
| 3,848,601 A | 11/1974 | Ma | |
| 4,059,115 A * | 11/1977 | Jumashev et al. | 606/82 |
| 4,697,586 A | 10/1987 | Gazale | |
| 4,736,738 A | 4/1988 | Liposvsek et al. | |
| 4,743,256 A | 5/1988 | Brantigan | |
| 5,571,109 A | 11/1996 | Bertagnoli | |
| 5,722,977 A | 3/1998 | Wilhelmy | |
| 5,800,437 A | 9/1998 | Gustilo et al. | |
| 5,957,836 A | 9/1999 | Johnson | |
| 6,096,038 A | 8/2000 | Michelson | |
| 6,110,175 A | 8/2000 | Scholl | |
| 6,174,311 B1 | 1/2001 | Branch | |
| 6,224,607 B1 | 5/2001 | Michelson | |
| 6,277,149 B1 | 8/2001 | Boyle | |
| 6,569,168 B2 | 5/2003 | Lin | |
| 6,666,866 B2 | 12/2003 | Martz et al. | |
| 6,746,454 B2 | 6/2004 | Winterbottom et al. | |
| 6,840,941 B2 * | 1/2005 | Rogers et al. | 606/79 |
| 6,911,045 B2 | 6/2005 | Shimp | |
| 2002/0068941 A1 | 6/2002 | Hanson | |
| 2003/0130667 A1 | 7/2003 | Lin | |
| 2004/0098129 A1 | 5/2004 | Lin | |
| 2004/0162562 A1 | 8/2004 | Martz | |
| 2004/0243242 A1 | 12/2004 | Sybert et al. | |
| 2004/0249377 A1 | 12/2004 | Kaes et al. | |
| 2005/0038511 A1 | 2/2005 | Martz et al. | |
| 2005/0240188 A1 | 10/2005 | Chow et al. | |
| 2006/0095043 A1 | 5/2006 | Martz et al. | |
| 2006/0149376 A1 | 7/2006 | Shimp et al. | |
| 2007/0073293 A1 | 3/2007 | Martz et al. | |

FOREIGN PATENT DOCUMENTS

| | | |
|---|---|---|
| WO | WO 01 62166 | 8/2001 |
| WO | WO 02 34144 | 5/2002 |

OTHER PUBLICATIONS

U.S. Appl. No. 60/397,232, filed May 19, 2002.

Posterior Lumbar Interbody Fusion Technique using the Variable Screw Placement Spinal Fixation System, John W. Brantigan et al. Spine: State of the Art Reviews, vol. 6, No. 1, pp. 177-198, Jan. 1992, Hanley & Belfus, Inc., Philadelphia, PA.

* cited by examiner

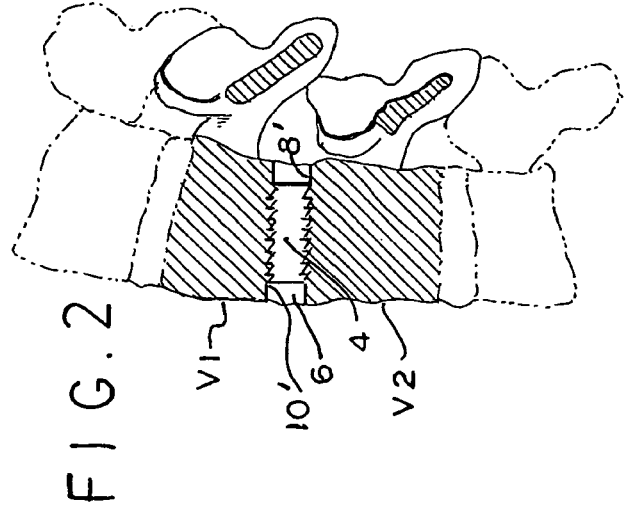
FIG. 2
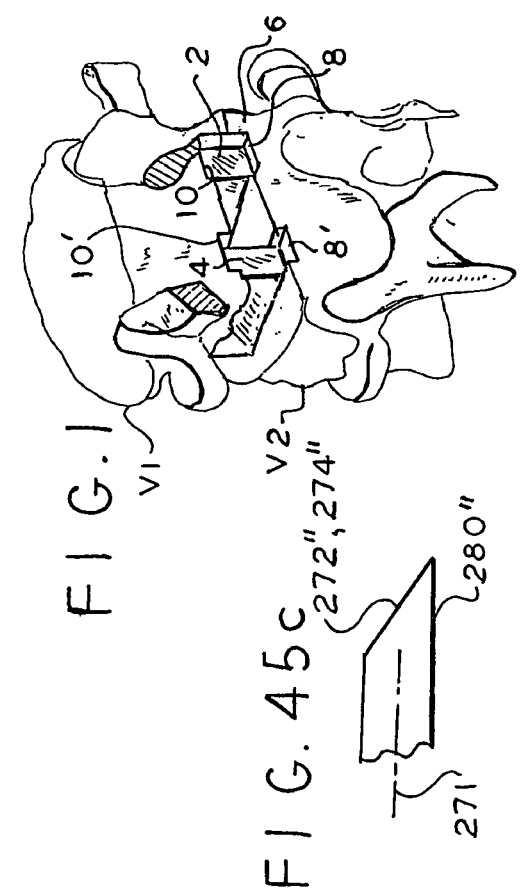
FIG. 1
FIG. 45c
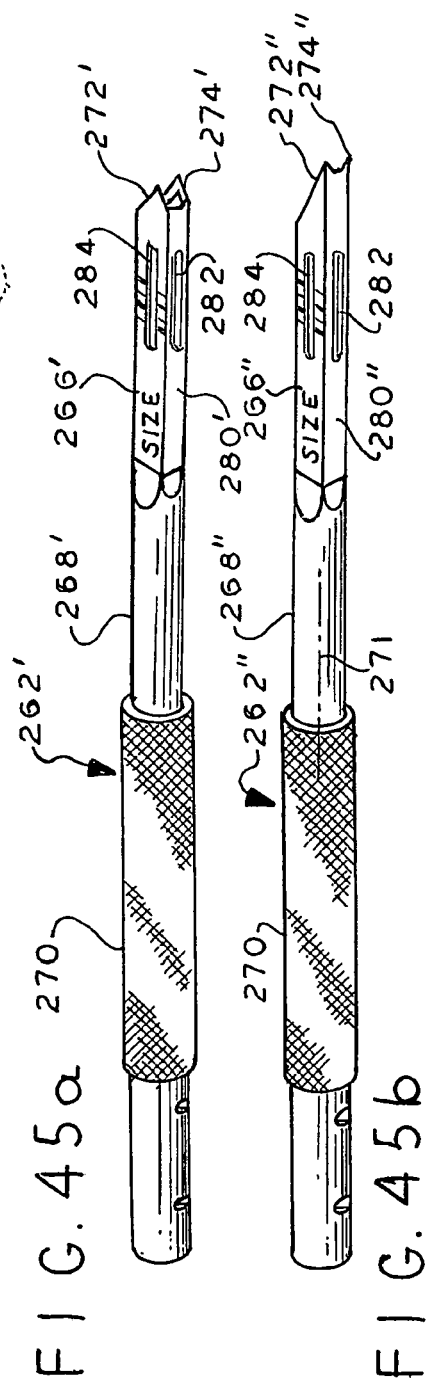
FIG. 45a
FIG. 45b

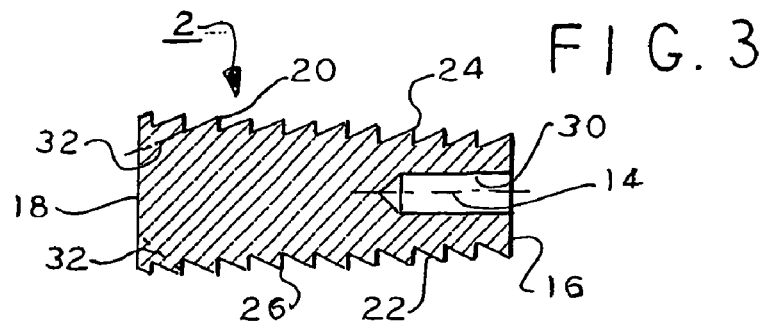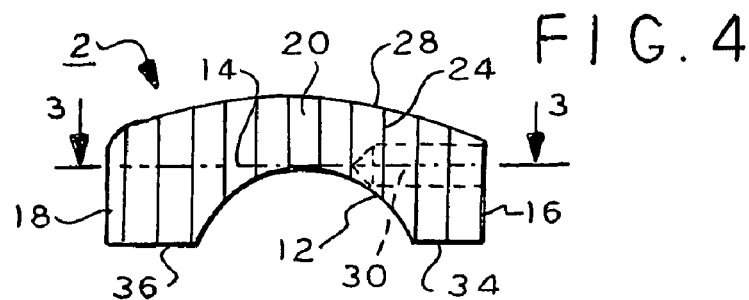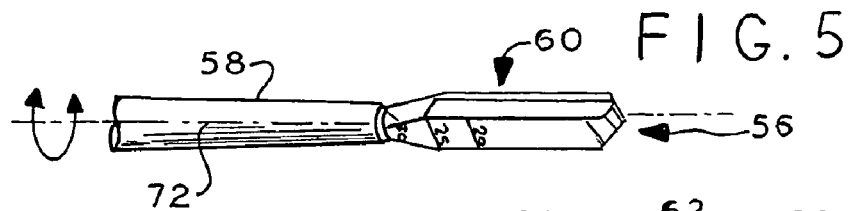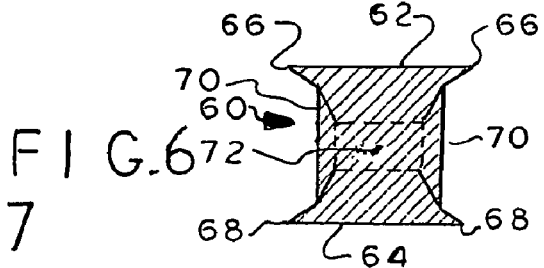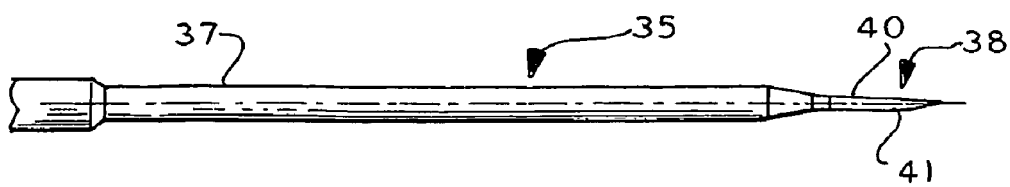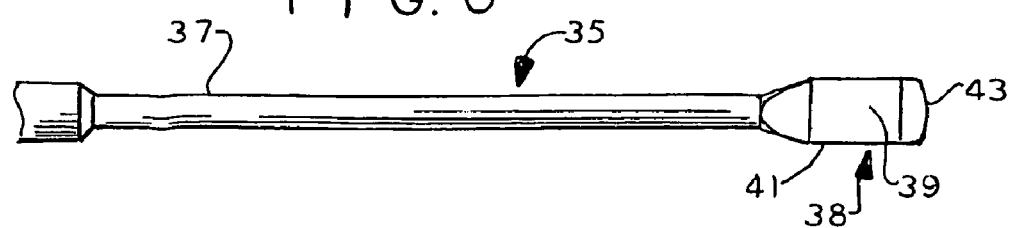

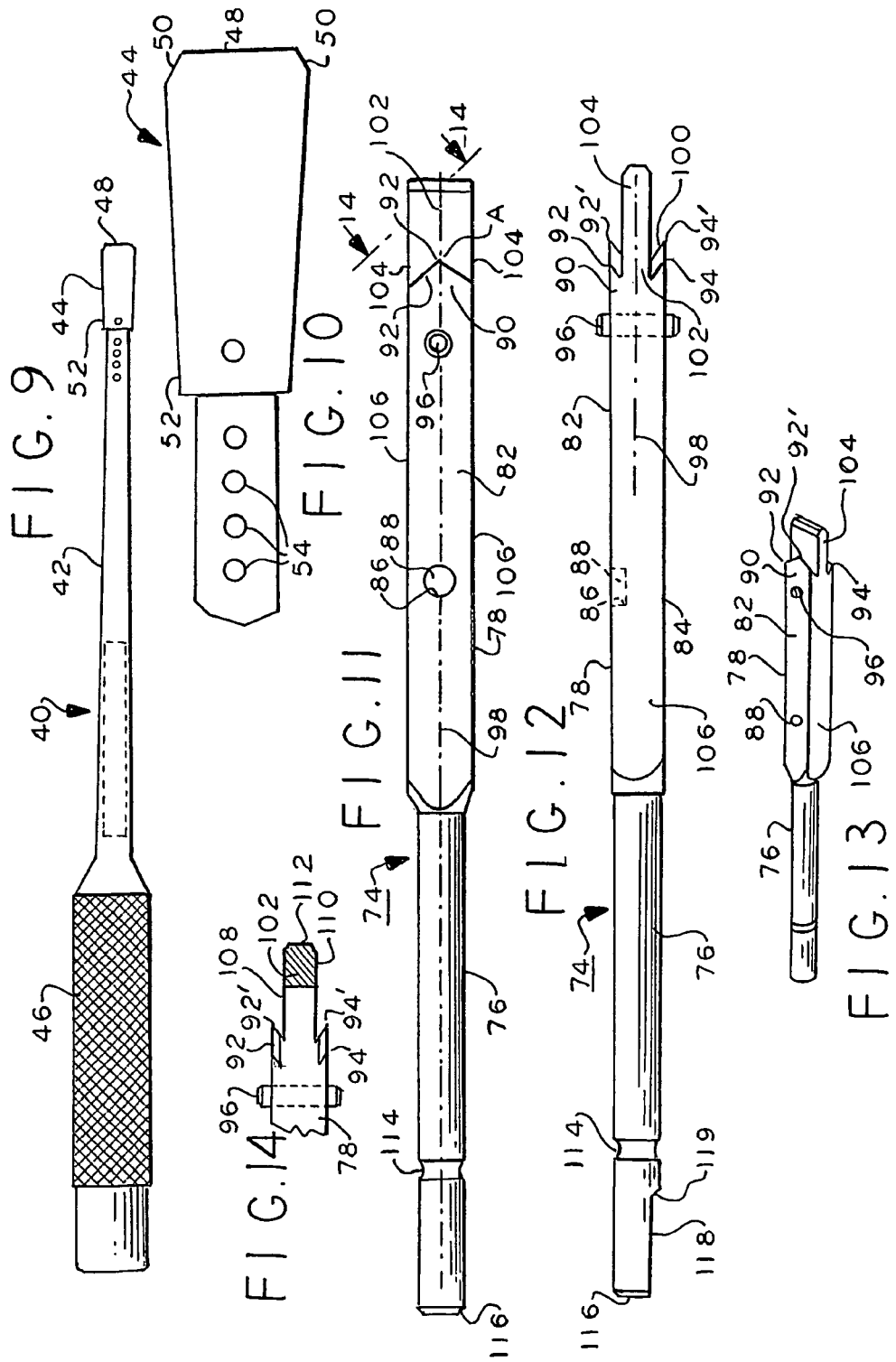

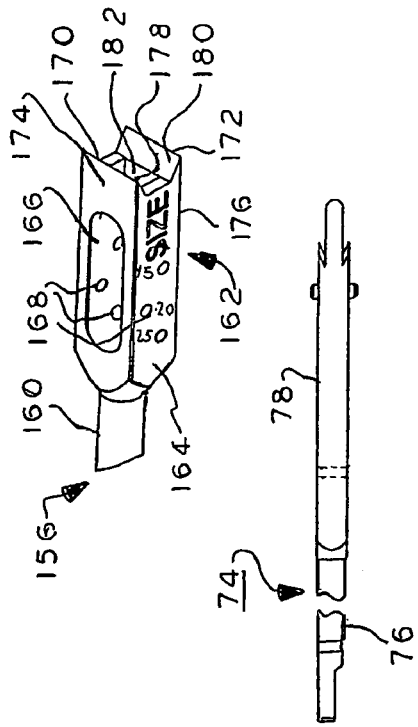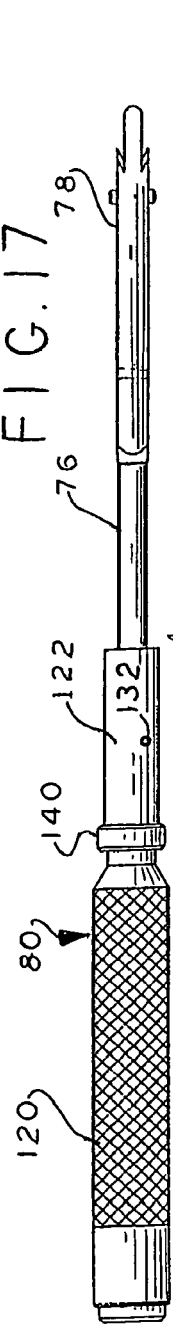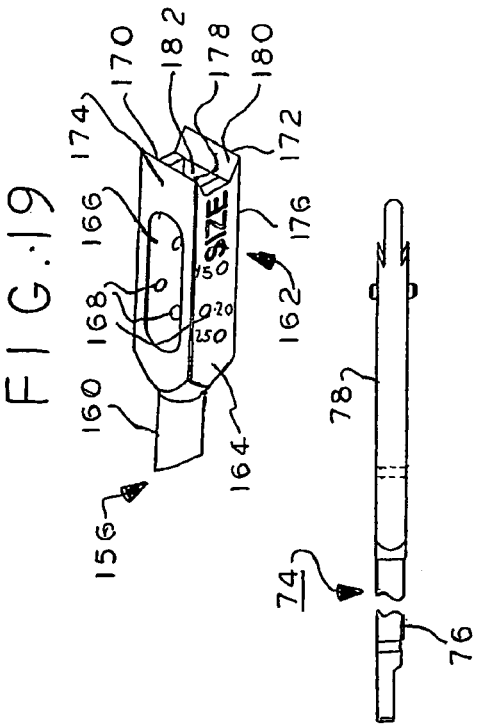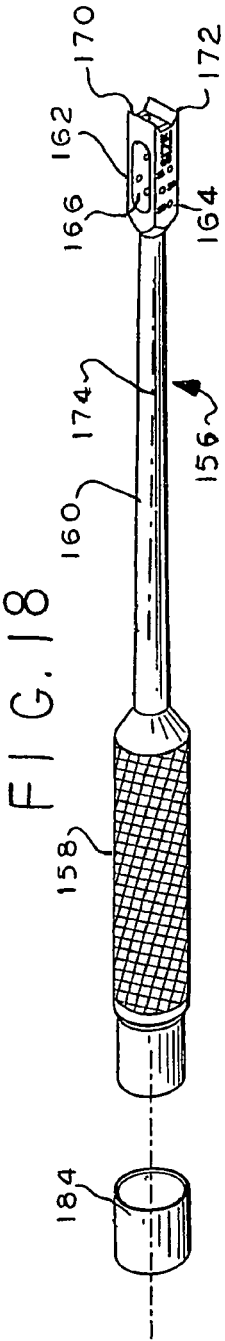

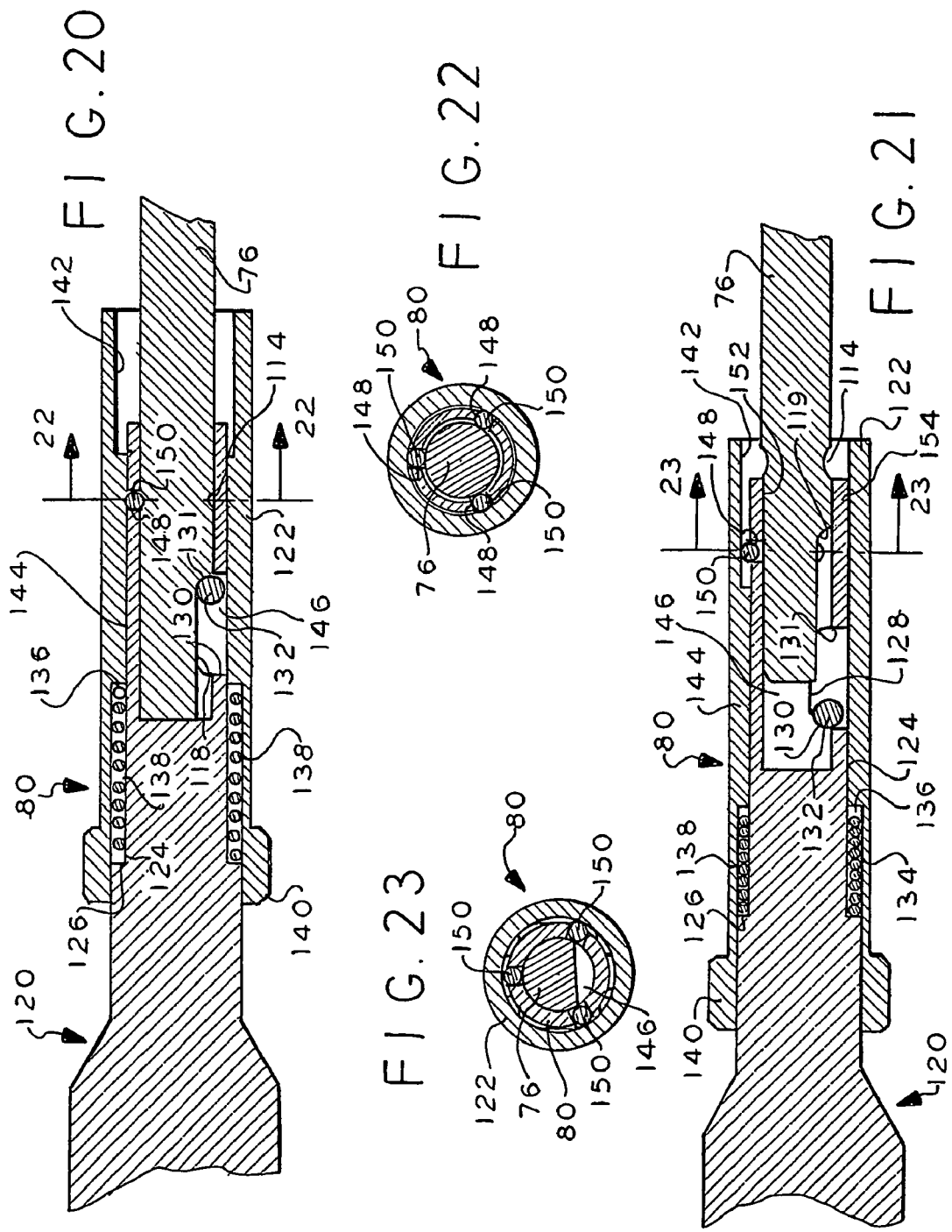

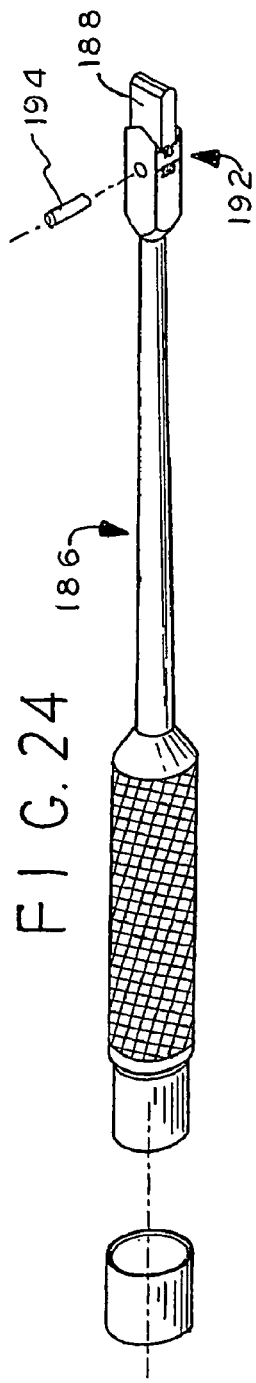
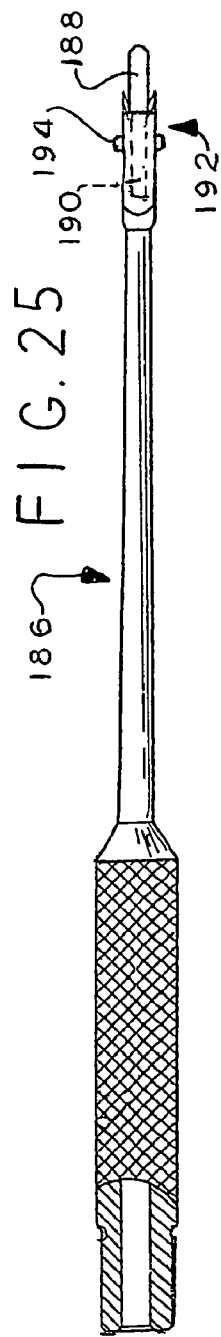
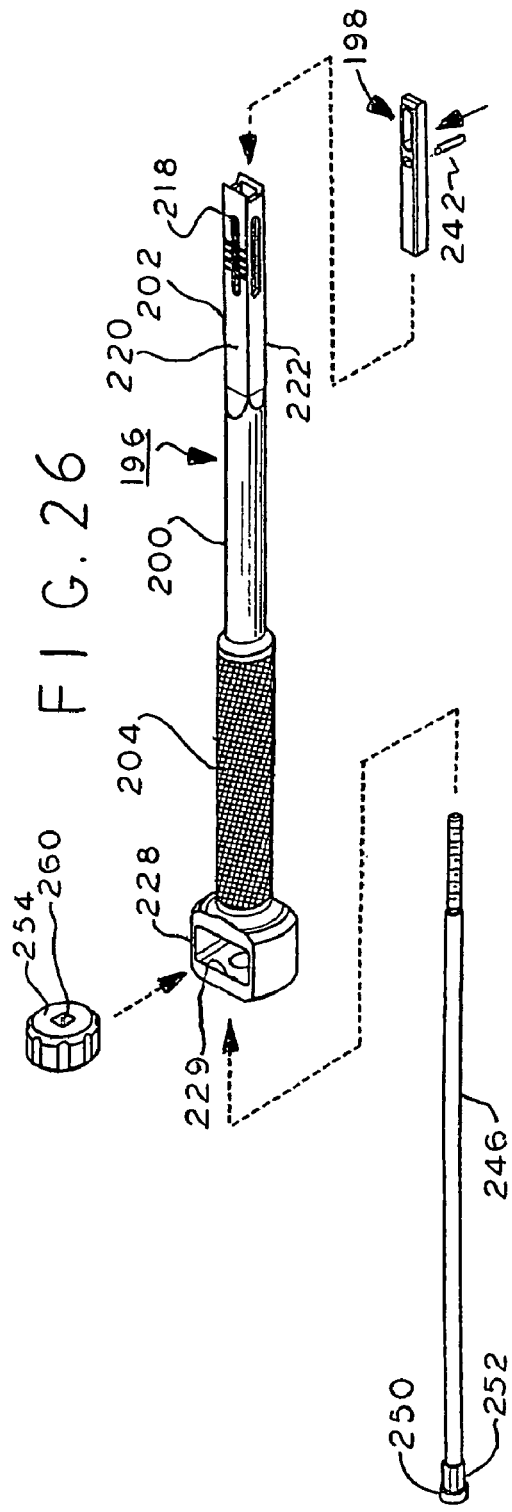

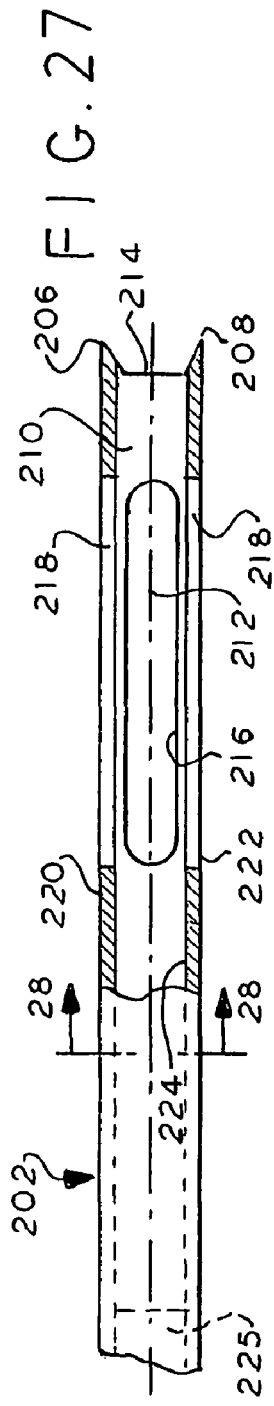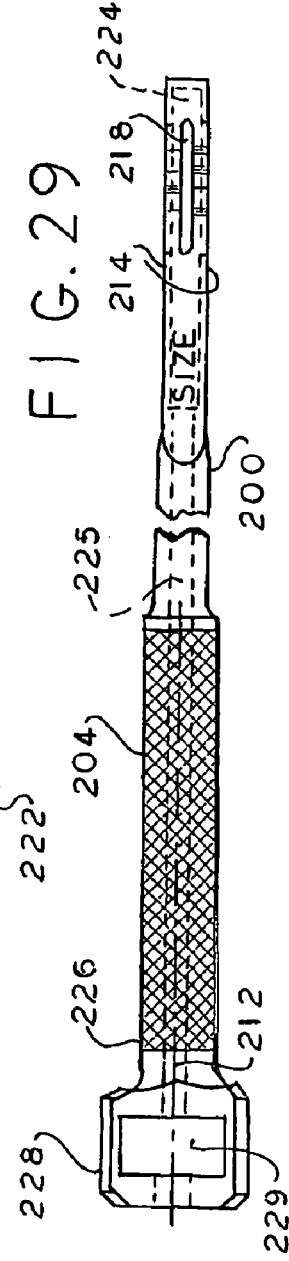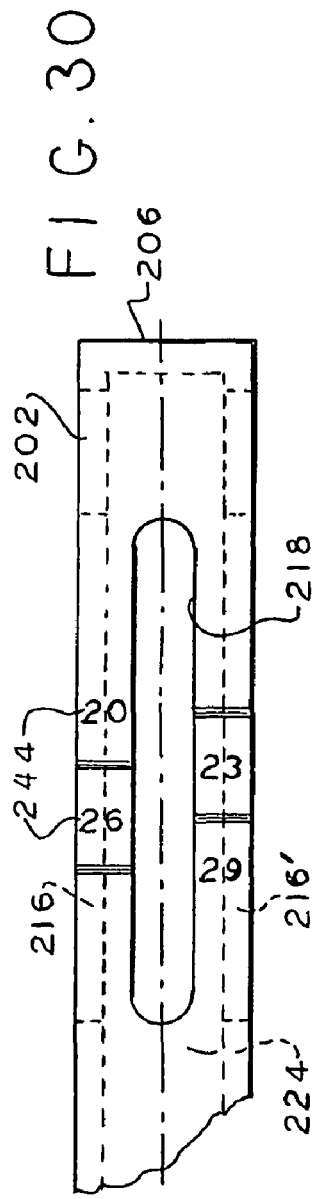

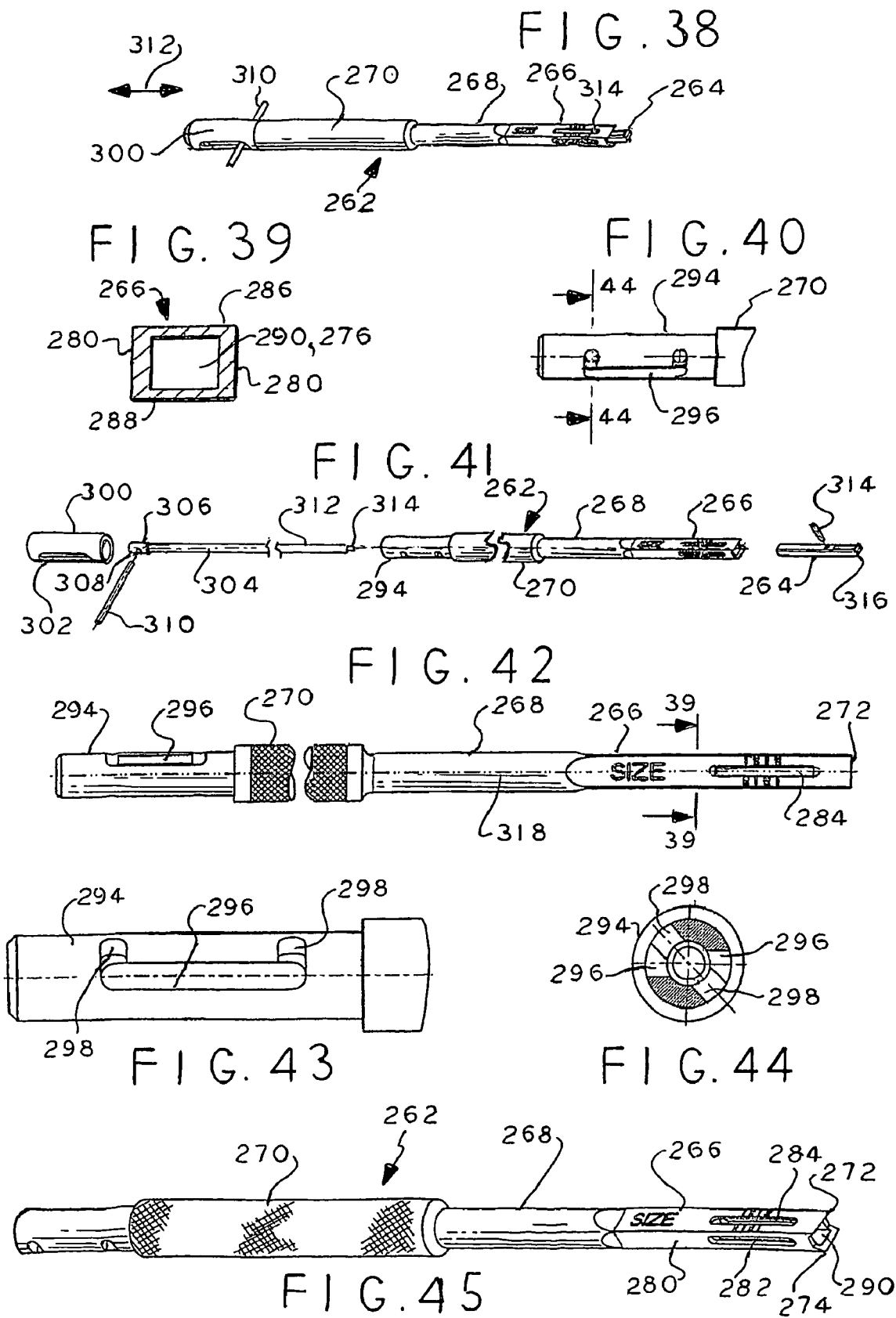

CHISELS AND PROCEDURE FOR INSERTION OF SPINAL IMPLANT IN A SPINAL DISC SPACE

This application claims the benefit of, is a continuation in part of and incorporates by reference in its entirety provisional application Ser. No. 60/397,232 filed Jul. 19, 2002.

This invention relates to spinal implant chisel tools and method of preparing the spinal disc space employing such chisels for insertion of implants into the intervertebral disc space.

Of interest is commonly owned U.S. Pat. No. 6,277,149 entitled Ramp-Shaped Intervertebral implant incorporated by reference herein.

Spinal implants, sometime referred to as grafts, are in wide use and typically comprise non-bone physiologically compatible metal or other non-bone materials or bone. Reference is made to the aforementioned patent for description of a bone implant. The method of preparing the site of the spine for spinal implant insertion involves a variety of tools and individual processes. The prior art is replete with different implants, implant insertion tools and procedures for insertion of spinal implants with such tools.

For example, U.S. Pat. No. 6,096,038 to Michelson discloses distraction tools for distraction of adjacent vertebrae, implants for insertion into the spine, drills for drilling the intervertebral site to prepare the site for implant insertion, other tools used for preparing the disc space by cutting bone, a driver extraction instrument for extracting an implant driver tool from the spinal disc space and generally discloses surgery for providing an integrated discectomy, fusion and interbody internal spinal fixation.

U.S. Pat. No. 6,174,311 to Branch discloses implants formed from donor bone for use in lumbar interbody fusion procedures and instruments for performing such procedures. Specific implants and instruments are disclosed for inserting the implants and for preparing the intervertebral space to receive the implants. Disclosed is a box chisel that has a hollow core that is somewhat rectangular.

Also disclosed is a plane scraper and a rotatable cutter. This latter cutter has multiple cutting arms defining a cavity therebetween for receiving cutting debris. Each arm has at least two cutting blades. The blades extend axially between the handle and the cutting end. The box chisel cutting edges are normal to the axial direction of the tool in a direction from the handle to the box cutter, whereas the rotating cutter cutting edges are parallel to the axial direction. In use, this rotating cutter tool cuts bone by rotation of the tool about its longitudinal axis.

In another embodiment, a box chisel is disclosed that has a depth stop to prevent the chisel from cutting deeper into the disc space than a predetermined depth and includes depth indicator marks to indicate the depth of penetration of the chisel. Implants and implant holders are also disclosed. This patent is incorporated by reference in its entirety.

U.S. Pat. No. 4,697,586 to Ganzale discloses a combined chisel-guide surgical instrument. The instrument is for performing osteotomy and other procedures on the human vertebra and comprises at least one longitudinally directed and movable chisel each including at least one front cutting edge for penetrating into the vertebra, a longitudinally directed guide including a front guide tip being locatable within intervertebral space for accommodating and directing the motion of the chisel cutting edges into the vertebra, a handle fixedly secured to rear extension of the guide for directing and placing the guide tip into the intervertebral space, a front impact block member connected to the rear extension of the chisel, an intermediate longitudinally directed cylindrical member connected to the rear end of the front impact block member, a rear impact cylindrical member fixedly connected to the rear end of the intermediate cylindrical member, and a longitudinally movable impact hammer accommodated by the intermediate cylindrical member.

The impact hammer causes forward penetration of the chisel front cutting edge to the desired penetration depth and the impact hammer impacts the cylindrical member to cause rearward retraction of the chisel and the handle causes rearward retraction of the guide tip from the disc space. The guide tip serves as a depth gauge. Surface extensions at the rear of the guide tip prevent penetration deeper than the anterior longitudinal ligament.

The chisel slides along a track surface on the guide. A two chisel embodiment is disclosed wherein one chisel penetrates one vertebra or two chisels are used to penetrate two vertebra. The impact hammer is operative with the one chisel or two chisels which are arranged in mirror image fashion to each other and are each disclosed as U-shape in one embodiment.

The guide tip is inserted into the disc space first. The chisel is then slid onto the handle and along a surface of the guide until the cutting edges rest on the dorsal aspect of the vertebral space. The impact hammer is used to insert the cutting edges into the vertebral plates. The chisel is withdrawn with the hammer leaving the guide tip inserted in the disc space. The tip is then withdrawn. In a two chisel mode, the guide tip is inserted first and then either or both chisels may be operated at the same time wherein the chisels may be driven one at a time or together. The guide tip is removed after the chisels are removed. The cutting edges are normal to the insertion direction and longitudinal axis of the instrument similar to a box chisel.

U.S. Pat. No. 4,736,738 to Lipovsek et al. discloses an instrument kit and method for performing posterior lumbar interbody fusion. The kit includes first and second chisels and first and second shafts, a retaining ring with a set screw, an extraction hammer, a tamper and a hook. The first and second chisels each have a U-shaped blade and a shoulder between the blade and shaft. The second chisel is larger than the first chisel to enlarge the groove made by the first chisel. A stop prevents the shaft from slipping through the intervertebral space. The shoulders limit the depth of penetration of the chisels. The first chisel is used first and then withdrawn from the disc space. Then the second chisel is inserted to enlarge the channel formed by the first chisel. The chisel edges are coplanar and at right angles to the longitudinal axis of the instrument shaft.

U.S. Pat. No. 695,783 discloses a coping tool or chisel having a contour of molding to be cut and comprises a double chisel. A guide piece slides in a vertical recess in a frame of a mortising machine. A guide piece and gauge piece supported by the guide piece are fixed to the chisel. When a corner of the mold engages the guide piece the required depth is cut.

U.S. Pat. No. 740,937 discloses a chisel with a forward end with projecting spurs having rounded cutting edges. A forward end portion has a cutting edge.

U.S. Pat. No. 3,848,601 to Ma et al. discloses an interbody fusion apparatus including an intervertebral mortising chisel with an inner drill bit. The sides of the chisel have stops. The cutting edges are coplanar and lie in a plane normal to the longitudinal axis of the shaft forming what Is generally referred to as a box chisel in that the edges of the chisel resemble a box shape.

U.S. Pat., No. 5,722,977 to Wilhelmy discloses a quadrilateral osteotome for use with a guide spacer. The guide spacer is inserted into the disc intervertebral space and while inserted, the chisel is then inserted to perform the bone cutting process guiding the chisel at this time. The guide spacer is received within the chisel hollow core and guides the chisel during its use. The chisel is shown as a box chisel.

U.S. Pat. No. 6,224,607 to Michelson discloses an instrument set that includes an extended guard for providing protected access to the disc space, and the adjacent surfaces of the adjacent vertebral bodies, a guide insertable into the guard, and a bone removal device such as a drill insertable into the guide.

The present inventors recognize a need for an improved chisel and procedure for preparing a spinal disc space for receiving a spinal fusion implant.

A chisel for preparing adjacent vertebrae for insertion of a spinal implant into the disc space defined by the vertebrae according to an aspect of the present invention comprises a handle and a shank having a longitudinal axis and distal and proximal ends, the handle being secured to the distal end. A bone cutting blade is attached to the shank proximal end and having a cutting edge lying in a plane for forming a channel in one of the vertebrae, the blade extending transverse to the longitudinal axis and having a bone cutting edge facing in a proximal direction, the blade edge being non-linear in shape and having an apex in top plan view, the cutting edge having first and second cutting coplanar portions that each taper in the proximal direction.

In one aspect, the first and second cutting edge portions taper toward each other terminating at the apex.

In one aspect, the first and second portions of the blade are symmetrical relative to the axis and the apex lies on the axis.

In a further aspect, the shank at the proximal end is solid with a rectangular cross section, the shank having peripheral top and bottom surfaces and peripheral first and second side surfaces, further including a solid rectangular chisel guide member one piece with and fixedly secured to the shank and extending from the shank proximal end coextensive with the outer side surfaces juxtaposed with and beyond the blade apex.

In a still further aspect, the blade has a top surface that is coextensive and coplanar with the shank top surface and a cutting edge that tapers distally toward the shank and toward the guide member.

In a further aspect, the shank has peripheral top and bottom surfaces, further including a projection extending from at least one of the top and bottom surfaces and spaced distally from the blade edge for abutting adjacent vertebrae during use of the chisel to limit the depth of penetration of the chisel into the vertebrae disc space.

In a further aspect, the projections each comprise a portion of a pin Inserted in a through bore in the shank.

In a further aspect, the shank has a groove and a shoulder adjacent to the distal end thereof, the handle including a quick release sleeve arranged to be releasable secured to the groove and shoulder.

In a further aspect, the sleeve includes a pin for mating with the shoulder to preclude relative rotation of the sleeve and handle to the shank.

In a further aspect, the handle includes a shaft portion with a plurality of balls arranged in annular array about the shaft portion for radially displacement in corresponding bores, the sleeve having a stepped bore having first and second segments for receiving the shaft portion along the axis, the first segment for allowing the balls aligned therewith to be radially aligned with and external said groove in a first axial position of the sleeve to permit the shank to be disengaged from the shaft portion and the second segment for urging the balls into the groove in a second axial position to releasably lock the shaft portion to the shank.

In a further aspect, including resilient means for resiliently urging the sleeve to a quiescent second position to normally lock the handle to the shank in the quiescent second position.

In a further aspect, the shaft portion and the sleeve have juxtaposed spaced shoulders, the resilient means comprising a spring between and abutting the shoulders.

In a further aspect, the shank has a hollow core at the proximal end facing in the proximal direction, further including a chisel guide member movably attached to the shank for selectively extending from the core in a direction toward the proximal end and retracting into the core in a direction toward the distal end.

In a further aspect, the guide member has a through slot, the shank including a pin fixed to the shank and movably attached to the guide member in the slot so that the guide member can axially displace in the core in opposite directions along the longitudinal axis toward and away from the proximal end.

In a further aspect, the pin protrudes from the shank to provide a visual indication of the depth of penetration of the chisel into the vertebral disc space and provides depth limit means for abutting at least one of the vertebrae forming a stop for the chisel.

In a further aspect, guide member displacement means are included for selectively manually respectively extending and retracting the guide member from and into the core.

Preferably the displacement means comprises a first rod attached to the guide member and having a rod portion extending into the handle, and a rod displacement arrangement coupled to the rod portion for axially displacing the first rod toward and away from the proximal end.

In a further aspect, the rod is releasably attached to the guide member.

In a further aspect, threads rotationally couple the rod to the guide member, and a knob is connected to the rod for rotating the rod relative to the guide member, the knob having a fixed axial position on the handle such that rotation of the knob displaces the guide member via the threaded engagement of the rod to the guide member.

In a further aspect, the knob is keyed to the rod to rotate the rod with rotation of the knob.

In a further aspect, the handle has a slot receiving the knob, the received knob for manual engagement by a thumb.

In a further aspect, the shank at the proximal ends has at least one through slot for receiving bone chips during use of the chisel.

In a further aspect, the rod displacement means includes a transversely extending second rod attached to the first rod at the first rod end distal the guide member and detent means attached to the handle for receiving the second rod for selectively releasably securing the second rod in guide member retracted and extended positions.

In a further aspect, the detent means comprises a slot in the handle for receiving the second rod, the slot having first and second axially spaced channels each for selectively receiving the second rod.

In a further aspect, a sleeve is included over the handle at the slot including a further slot juxtaposed with the handle slot In a method for preparation of a disc space for insertion of a spinal implant into the disc space between adjacent vertebrae, the steps according to a further aspect of the present invention comprises initially removing a first portion of at least one of two adjacent vertebrae of the disc space with a first chisel with an extended guide member to form at least one partial channel in the at least one vertebra, the guide member for bearing against the adjacent vertebrae and guiding the chisel during the removing; and then removing a further deeper second portion of the at least one adjacent vertebrae with a second chisel guided by first channel portion, the second chisel having no guide member, to form the at least one partial channel into at least one complete channel for receiving a spinal implant inserted into the disc space, the further portion being aligned with and extending the at least one channel to a depth into the disc space an amount sufficient to form the complete channel.

In a further aspect, the method includes forming the at least one partial channel and the at least one complete channel in each of the adjacent vertebrae with the same chisel.

In a further aspect, the removing a further portion of the at least one adjacent vertebrae with a second chisel includes retracting the guide member of the first chisel into the first chisel to form the first chisel into the second chisel.

In a further aspect, the method includes the removing a further portion of the at least one adjacent vertebrae with a second chisel includes removing the first chisel from the formed at least one partial channel in the at least one vertebra and then inserting the second chisel into the formed at least one partial channel wherein the at least one partial channel guides the second chisel during the insertion.

IN THE DRAWING

FIG. 1 is an isometric view of a portion of the lumbar spine with a pair of implants inserted posteriorly into the disc space according to a process of the present invention;

FIG. 2 is a side elevation view of the spine of FIG. 1;

FIG. 3 is a side sectional elevation view of a representative spinal implant that may be inserted into the disc space prepared by the procedure of the present invention;

FIG. 4 is a plan view of the implant of FIG. 3;

FIG. 5 is an isometric view of a rotating scraper which may be used in the process of the present invention;

FIG. 6 is a sectional end elevation view of the scraper of FIG. 5 showing the blade portion of the scraper;

FIGS. 7 and 8 are side and plan elevation views of a paddle type distractor that may be used in the process of the present invention;

FIGS. 9 and 10 are respective side elevation views of a trial useful in the procedure of the present invention wherein FIG. 10 is a more detailed view of the measuring end of the trial of FIG. 9;

FIG. 11 is a top plan view of a chisel according to an embodiment of the present invention with a fixed guide member;

FIGS. 12 and 13 are respective side elevation and isometric views of the chisel of FIG. 11;

FIG. 14 is a side elevation sectional fragmented view of the chisel of FIG. 11 taken along lines 14-14;

FIG. 15 is an isometric view of a quick release handle for use with the chisels of FIGS. 11-13 and FIGS. 16-17;

FIG. 16 is an exploded side elevation view of a chisel according to a further embodiment of the present invention;

FIG. 17 is a side elevation view of the assembled chisel of FIG. 16;

FIGS. 18 and 19 are isometric views of a chisel and chisel tip end showing two blade cutting edges of a chisel for use with a process according to a further embodiment of the present invention FIGS. 20 and 21 are respective side sectional fragmented elevation views of the assembled handle and chisel of FIG. 17 in respective handle locked and unlocked states;

Figure 31:
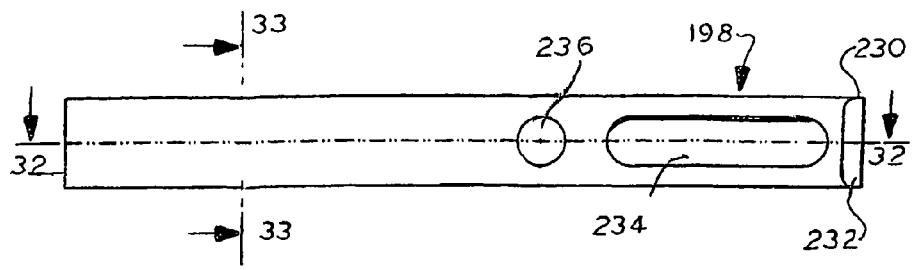
Figure 32:
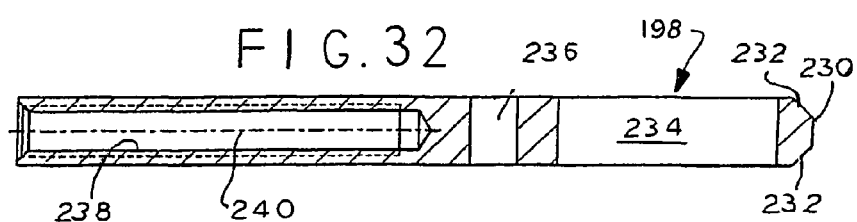
Figure 34:
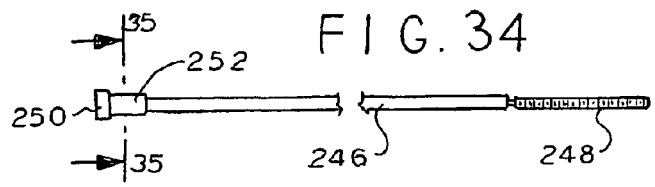
Figure 33:
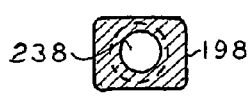
Figure 35:
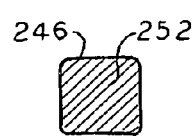
Figure 36:
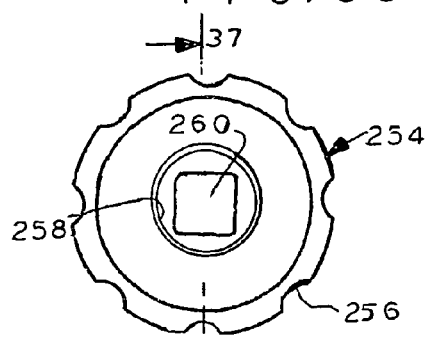
Figure 37:
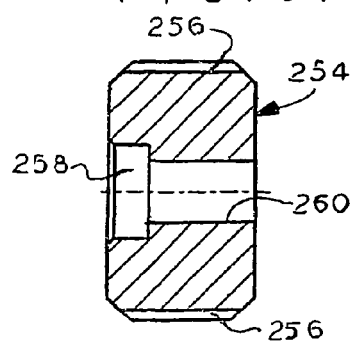
Figure 46:
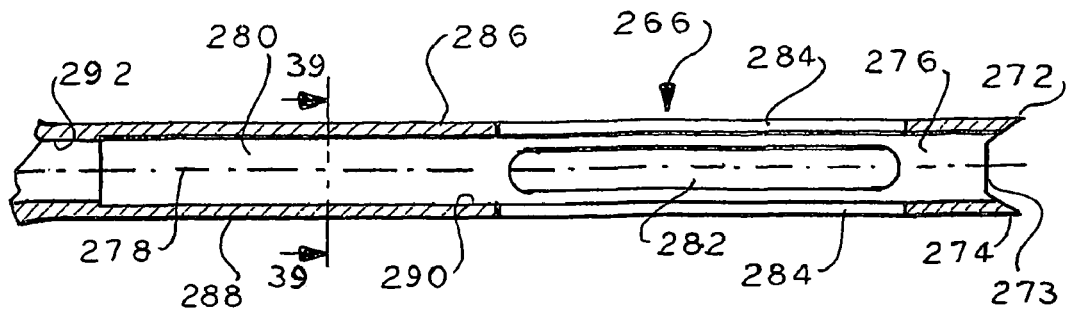
Figure 47:
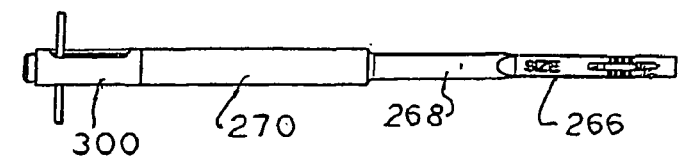
Figure 48:
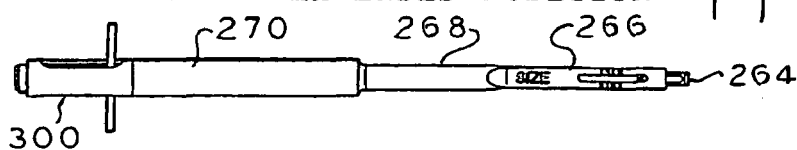
Figure 49:
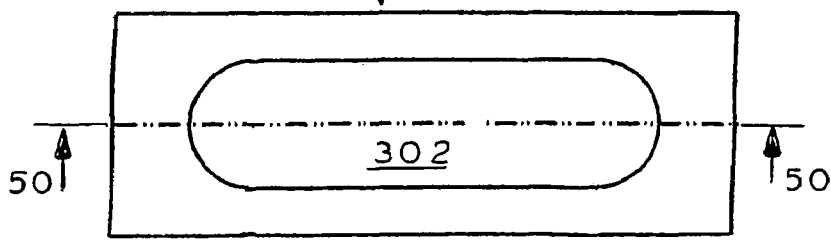
Figure 50:
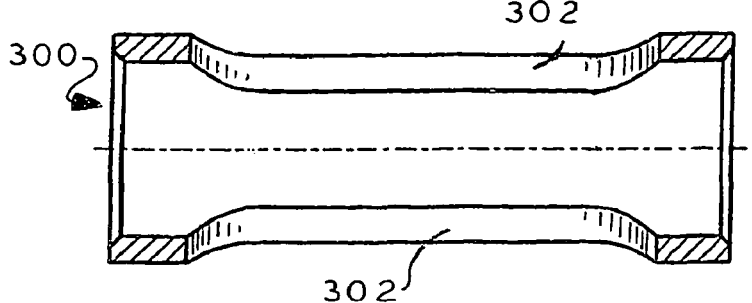
Figure 51:
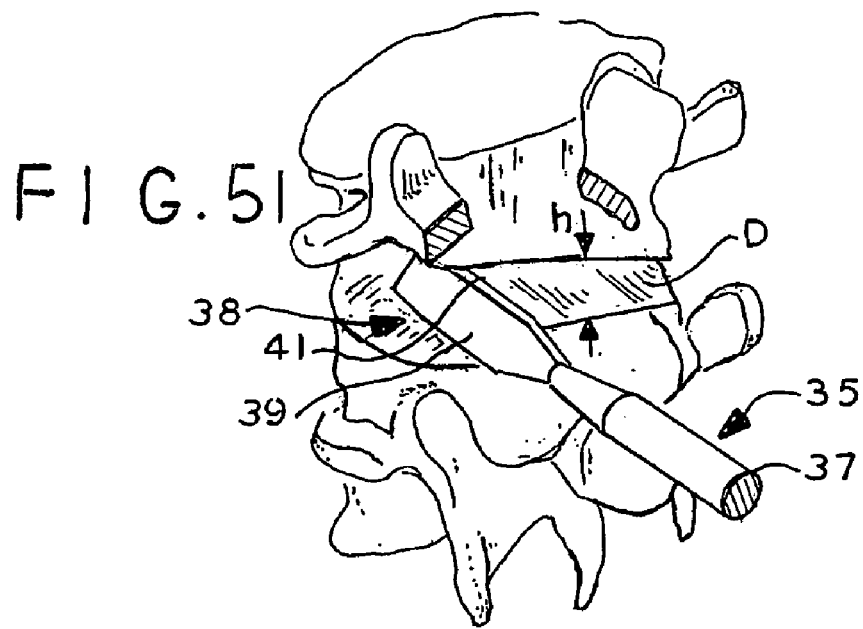
Figure 52:
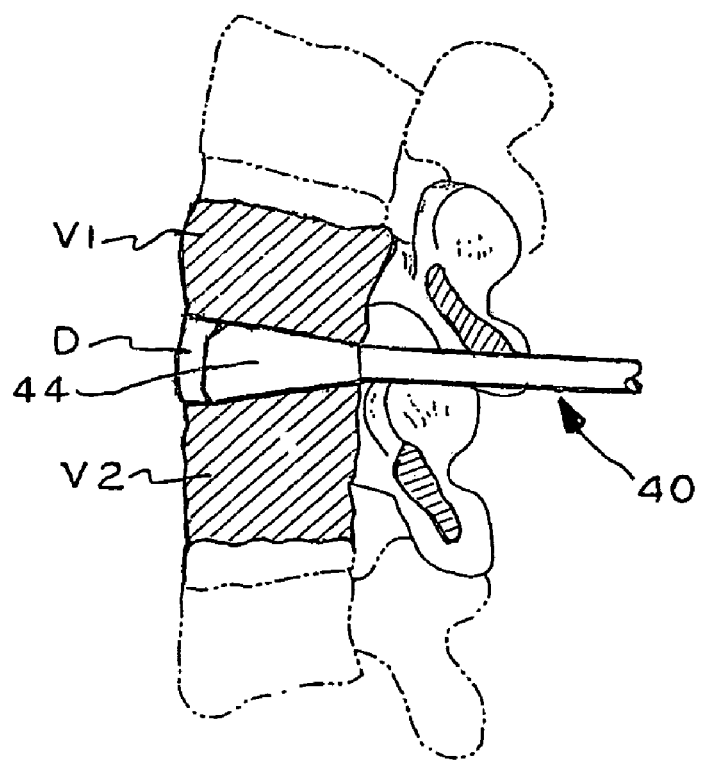
Figure 53:
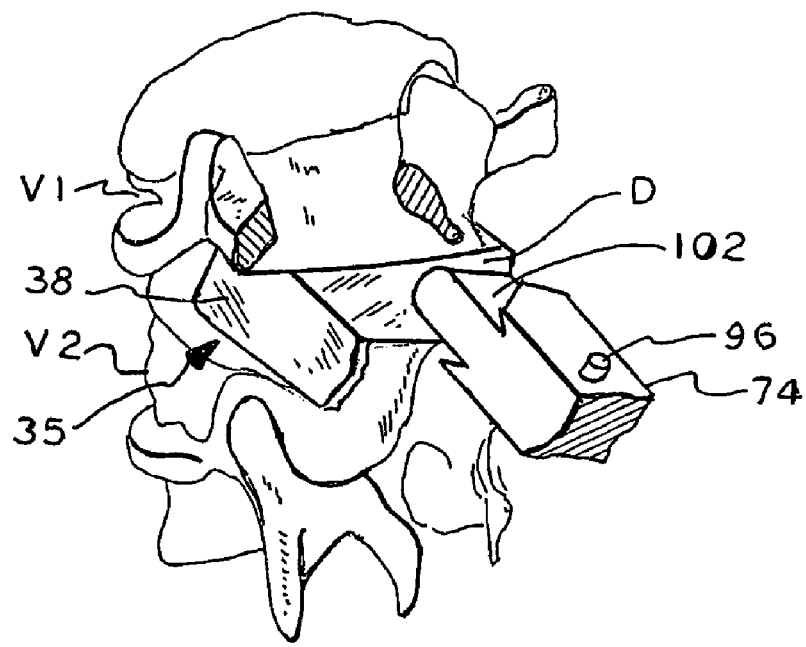
Figure 54:
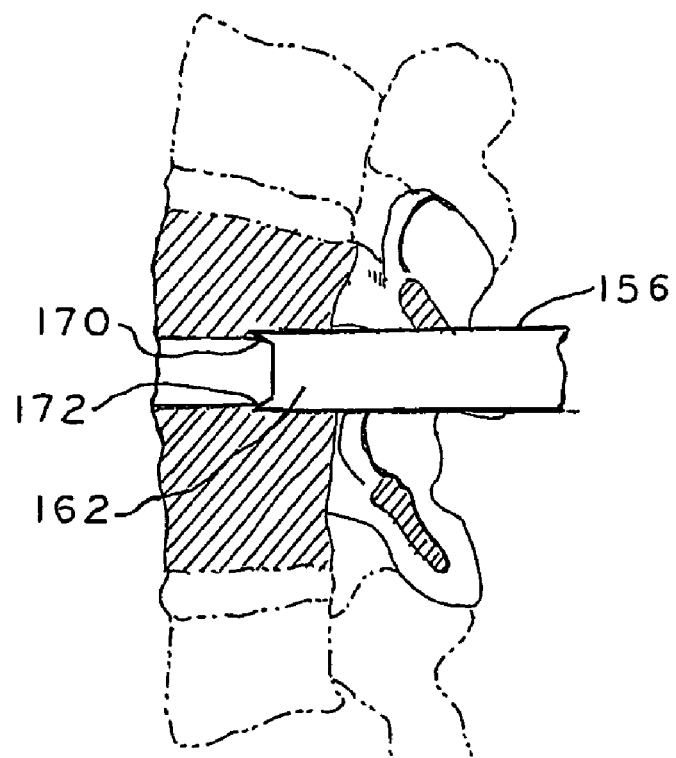

FIGS. 22 and 23 are respective sectional views of the embodiments of FIGS. 20 and 21 taken at respective lines 22-22 and 23-23;

FIGS. 24-25 are respective isometric AND side elevation and views of a chisel with a fixed guide member according to a further embodiment of the present invention;

FIG. 26 is an isometric exploded view of a chisel with a retractable guide according to a further embodiment;

FIG. 27 is a fragmented side elevation partially in section of a chisel tip portion of the chisel of FIG. 26;

FIG. 28 Is a sectional end elevation view of the portion of FIG. 27 taken at lines 28-28;

FIG. 29 is a fragmented side elevation view of the handle, shaft and chisel portions of the chisel of FIG. 26;

FIG. 30 is a more detailed side elevation view of the chisel cutting end of the chisel of FIG. 29;

FIG. 31 is is a side elevation view of the chisel guide member of the chisel of FIG. 26;

FIG. 32 is a sectional elevation view of the member of FIG. 31 taken at lines 32-32;

FIG. 33 is an end elevation sectional view of the member of FIG. 31 taken at lines 33-33;

FIG. 34 is a fragmented side elevation view of a threaded rod for use with the chisel of FIG. 26;

FIG. 35 is a sectional view of the rod of FIG. 34 taken at lines 35-35;

FIG. 36 is an end elevation view of the knob used with the chisel of FIG. 26;

FIG. 37 is a sectional view of the knob of FIG. 36 taken at lines 37-37;

FIG. 38 is an isometric view of a chisel according to a further embodiment of the present invention;

FIG. 39 is a sectional elevation view of the chisel portion of FIG. 46 taken along lines 39-39;

FIG. 40 is a fragmented side elevation view of a portio of the handle of the chisel of FIG. 38;

FIG. 41 is an exploded isometric view of the chisel of FIG. 38;

FIG. 42 is a fragmented top plan view of the chisel shaft of FIG. 38;

FIG. 43 is a more detailed side elevation view of the handle portion of the chisel of FIG. 41;

FIG. 44 is a sectional elevation of the embodiment of FIG. 40 taken along lines 44-44;

FIG. 45 is an isometric view of the shaft of the chisel of FIG. 42;

FIG. 45a is an isometric view of shaft of a chisel similar to the shaft of the chisel of FIG. 45 except the shaft of FIG. 45a has V-shaped cutting edges the same as the cutting edges of the chisel of FIGS. 11-13 and is arranged to receive a retractable guide as shown for example for the chisel of FIG. 38 rather than a fixed guide as shown in the embodiment of FIGS. 11-13;

FIG. 45b is an isometric view of shaft of a chisel similar to the shaft of the chisel of FIG. 45 except the shaft of FIG. 45a has cutting edges that are inclined relative to the longitudinal axis of the shaft and is arranged to receive a retractable guide as shown for example for the chisel of FIG. 38;

FIG. 45c is a top plan view of the blades of the chisel of FIG. 45b;

FIG. 46 is a fragmented sectional side elevation view of the chisel end of the chisel of FIG. 45;

FIGS. 47 and 48 are respective side elevation view of the chisel of FIG. 38 showing the chisel with its guide member retracted and extended;

FIG. 49 is a side elevation view of the sleeve portion of the chisel of FIG. 41;

FIG. 50 is a sectional elevation view of the sleeve of FIG. 49 taken along lines 50-50;

FIG. 51 is an isometric view of a portion of the human spine during the spinal preparation process for receiving the spinal implants of FIGS. 1 and 2;

FIG. 52 is a side elevation view of the human spine showing a trial tool used to determine the size of the disc space after preparation of the disc space prior to insertion of the implant;

FIG. 53 is an isometric view of the human spine showing a later chiseling step using the chisel of FIG. 11 in the process of FIG. 51; and FIG. 54 is a side elevation view of a chiseling step in the spinal disc preparation process using the chisel of FIGS. 18 and 19 in a step subsequent to the step of FIG. 53.

In FIGS. 1 and 2, two spinal implants 2 and 4 of the configuration of the implant of FIGS. 3 and 4, are shown implanted into the disc space 6 between adjacent vertebrae V1 and V2. The implants 2 and 4 are mirror images of each other and a description of one is representative. The disc space 6 has been prepared for receipt of the implants according to the procedure described later herein. The implants 2 and 4 are each located in corresponding channels 8 and 10, and 8' and 10', respectively, prepared according to the procedure to be described. The implants 2 and 4 have been inserted from the posterior approach. In the alternative, these implants may be inserted from the anterior, the antereo-lateral or any other approach relative to the spine as desired.

A further tool utilized in inserting the implants 2 and 4, are trials which determine the size of the disc space between the channels 8 and 10 or 8' and 10', FIGS. 1 and 2.

In FIGS. 3 and 4, representative implant 2 is formed of cortical bone in a known manner, for example, as disclosed in the aforementioned commonly owned and Branch patents. The outer surfaces are machined to the shape as shown. The implant has a longitudinal axis 14 and terminates at opposite ends in planar respective posterior and anterior end surfaces 16 and 18. The implant has serrated opposing surfaces 20 and 22 for engaging the associated adjacent vertebra.

The serrations on surfaces 20 and 22 are formed by parallel grooves forming respective saw teeth 24 and 26. The side wall surface 28 opposite the cavity 12 is convex arcuate. The implant may have tapered surfaces 20 and 22 at the anterior end at surface 18 as shown by dashed lines 32. A bore 30 may be formed in surface 16. Bore 30 receives an insertion tool to assist in insertion of the implant. The bore 30 may be smooth walled or threaded to receive an insertion tool rod (not shown). The opposing surfaces 20 and 22 are wedge shaped to conform to the lordotic shape of the intervertebral space tapering to the widest region at the anterior end of the implant. Side surfaces 34 and 36 are flat and coplanar.

In FIGS. 7 and 8, a paddle distractor 35 of known configuration comprises a shank 37 and the distractor working end 38. End 38 has a relatively wide flat surface 39 and a relatively narrow side wall surface 41. The tip 43 may taper somewhat. A similar distractor is disclosed in U.S. Pat. No. 5,957,836 to Johnson and in an article entitled Posterior Lumbar Interbody Fusion Technique using the Variable Screw Placement Spinal Fixation System by John W. Brantigan et al. Spine: State of the Art Reviews, Vol. 6, No. 1, pages 177-198 and in particular at page 181, January 1992, Hanley & Belfus, Inc., Philadelphia, Pa, wherein the tool is referred to as a spreader, both documents being incorporated by reference herein.

A further tool used during the implant insertion process is a trial such as trial 40, FIG. 9. The trial 40 has a shank 42, a measuring tip 44 and a handle 46. The tip 44, FIG. 10 has a body 46 which is wedge shaped to match the wedge configuration of the implants 2 and 4 and so on. The anterior measuring end 48 is tapered at insertion chamfers 50 which facilitate the insertion of the trial into the disc space in the posterior direction. The tip 44 tapers and converges toward the posterior end 52 and matches the taper of the implants such as implants 2 and 4, for example. Holes 54 are utilized to assist the surgeon in visually identifying the depth of insertion of the trial tip 44. The tip 44 engages the channels 8, 10, or 8', 10' across the prepared disc space 6, FIGS. 1 and 2. The implants, distractor and trial are available is sets of matching dimensions so that a given distractor and trial dimensions correspond generally to a given implant dimension. The trial is used to determine the size of the disc space between the channels 8, 10 and the surgeon then selects the implant of a given dimension that matches the fit with the trial. The distractors are made in sets of differing dimensions also to assist in utilizing the selected dimensions of the associated trial. This will all be explained more fully below in connection with the procedure for preparing the disc space.

In FIGS. 5 and 6, a further tool utilized in preparing the disc space is a rotatable scraper 56. Scraper 56 has a shank 58 connected at one end to a handle (not shown) and a vertebrae scraping tip 60 at the other end. In FIG. 6, the tip 60 has two opposing planar surfaces 62 and 64. Surface 62 terminates in bone cutting edges 66 at opposite sides of the tip. Surface 64 terminates in bone cutting edges 68 at opposite sides of the tip. A channel 70 is between each of edges 66 and 68 on each side of the tip 60. During use, the scraper 56 is rotated about its longitudinal axis 72, FIG. 5.

In FIGS. 11-17 a chisel 74 according to a first embodiment is shown. Chisel 74 has a shank 76 and a chisel end 78. A quick release handle 80, FIGS. 15-17, is releasably attached to the shank 76. In FIGS. 11-13, chisel 74 end 78 is a solid rectangular metal, preferably stainless steel. The shank 76 is circular cylindrical. The end 78 has opposing parallel planar top and bottom respective surfaces 82 and 84. A cylindrical bore 86 is formed in the surface 82. The bore 86 receives a color coding disc 88 which identifies the dimensions of the blades 92 and 94 at the chisel tip 90. A pin 96 passes through a through bore in the chisel end 78 extending beyond each of the top and bottom surfaces 82 and 84.

The blades 92 and 94 are identical mirror images of each other and are juxtaposed with each other. The blades have cutting edges 92' and 94' coplanar with the top and bottom surfaces 82 and 84, respectively. In this embodiment, the edges 92' and 94' are each non-linear in that they are V-shaped in plan view with the center of the Vee lying on a plane containing the longitudinal axis 98, FIG. 11. Each edge 92', 94' has two portions that are inclined to the plane normal to the drawing sheet containing the axis 98 at equal angles at an acute angle. The edges 92' and 94' terminate at an apex A on the plane containing the longitudinal axis 98. The sides 100 of the edges of the blades 92 and 94 taper toward the plane that is normal to the drawing sheet and which plane contains the longitudinal axis 98, FIG. 12. The sides 100 are preferably symmetric with that plane. In the alternative, the angles formed by the edges 92' and 94' with the axis 98 need not be equal. In a further alternative, the apex of the V may be inversely located to that shown so that it forms a V-shaped channel with the edge portions and the two sides of the V taper toward the distal end and toward the apex. In this embodiment, the two edge portions taper from the apex toward the chisel side walls and toward the proximal end.

In the alternative, the edge of each blade may be U-shaped in plan view similar to the view of FIG. 11. The U-shape is thus curved and may join the sides 104 in a gradual taper. In this case, the U-shaped edges have an apex that is curved rather than pointed in plan view. Thus a tangent to opposite sides of the U intersect the corresponding side walls such as walls 104, FIG. 11, of the chisel at an acute angle. The U shape edge may be symmetrical or asymmetrical about axis 98, FIG. 11. Also the sides of the U terminate centrally at the apex of the U. As used herein and in the claims the term "blade" is intended to include at least the cutting edge(s) of the chisel.

In a further alternative, the cutting edge may comprise a series of V or U-shaped cutting edges to form a generally saw tooth pattern in the plan view. These various shaped cutting edges generally may be non-linear, i.e., curved as in U-shaped, V-shaped or other non-linear shape in top plan view as seen in FIG. 11, for example. Thus the term non-linear edge means that the cutting edge from end to end, i.e., from side wall 104 to opposite side wall 104, has at least a non-linear portion (a change in direction) in the plan view of the edge as edge 92', FIG. 11. That non-linear portion may include linear sub-portions such as formed by edge portions on opposite sides of the apex of a V-shaped edge, FIG. 11.

Where the term calling for the edge to intersect the longitudinal axis is used, the term edge refers to the plane containing the edge, such as the plane of the drawing sheet, FIG. 11. Thus the edge 92', FIG. 11, lying in the plane of the drawing sheet of FIG. 11, intersects the plane containing the longitudinal axis 98, the latter plane being normal to the drawing sheet. The edges (or the linear portions of the edges as in V-shaped edges) of all of the chisels disclosed herein lie in and define a plane such as the edges 92', 94', FIGS. 11 and 12. That plane is normal to the plane of the drawing sheet in FIG. 12 and parallel to the drawing sheet in FIG. 11. The non-linear edges may also be undulating or other shapes. A U-shaped edge (not shown) thus has a tangent thereto that intersects the sides of the chisel such as sides 106, FIG. 11. The term "tapering edges" refers to both linear and curve edges.

A guide member 102 extends from the end 78 beyond the edges of the blades 92 and 94 and is one piece integral with the end 78. The guide member 102 has opposite sides 104 that are coextensive and coplanar with the sides 106 of the end 78. The guide member 102 has parallel top and bottom surfaces 108 and 110, respectively, FIG. 14. The member 102 has chamfers at the top and bottom surfaces thereof at the leading edge 112 to facilitate insertion into the disc space between adjacent vertebrae.

The shank 76, FIGS. 11 and 12, has an annular groove 114 at the distal end 116 and a flat radially inwardly extending step 118 in the region between the groove 114 and the end 116. The step 118 has a shoulder 119. The shank 76 at the groove 114 and step 118 receives quick release handle 80, FIGS. 15-17 and 20-23.

The quick release handle 80 includes a handle portion 120 and an axially movable sleeve 122. In FIGS. 20 and 21, the handle portion 120 has a circumferential radial inward step 124 forming an axially facing shoulder 126. The step 124 terminates in a further radial inward planar step 128 having an axially facing shoulder 130. A pin 132 is attached by press fit to the sleeve 122 and is captured to the handle portion in channel 128 by shoulders 130 and 131.

The sleeve 122 has radially outwardly formed steps 134 and 142 forming an intermediate region 144 of smaller diameter than that of steps 134 and 142. Step 134 has a shoulder 136. A coil compression spring 138 is secured between the step 124 of the handle portion 120 and step 134 of the sleeve 122 and is captured between shoulders 126 of the handle portion 120 and 136 of the sleeve 122. The sleeve 122 has a collar 140.

With the sleeve 122 engaged with the shank 76 as shown in FIGS. 20 and 21, the pin 132 is adjacent to the step 118 on the shank 76 and is located in the channel 128 of the handle portion 120.

The pin 132 abuts the flat surface of the step 118 of the shank 76 and the base surface of the channel 128 of the handle portion. The pin 132 prevents relative rotation of the shank 76 to the handle portion 80.

The handle portion 80 has a bore 146 that axially receives the shank 76. A set of three radial through holes and counter bores 148 are in the handle portion 80 in communication with the bore 146. Three stainless steel balls 150 are each free floating in a corresponding counter bore 148, but captured to the handle portion 80 by smaller through holes on the radial inside of the counter bores and by sleeve 122 on the radial outside of the counter bores. The balls selectively can protrude radially inwardly into the bore 146, FIG. 20, from the counter bores 148, or radially outwardly from the counter bores 148, FIG. 21.

The balls 150, in the position of FIG. 21, are flush with the outer surface 152 of the shank 76. In this position the balls 150 protrude radially outwardly from the counter bores 148. The balls, in the position of FIG. 20, protrude radially inwardly from the counter bores 148 engaging the annular groove 114 on shank 76.

In operation of the quick connect handle, the sleeve 122 is in the normal position, FIG. 16, with the balls protruding radially inwardly from the counter bores 148 into bore 146 by the inner surface of the intermediate region 144. To engage shank 76, the sleeve 122 is pulled by hand toward the handle portion 120 SO that the balls are free to protrude radially outwardly from the handle portion 80 segment 154 surrounding the bore 146 into step 142. The shank 76 is inserted into the bore 146 as shown in FIG. 21. The shank 76 outer peripheral surface forces the balls radially outwardly into the step 142 in this position. When the shank 76 is fully inserted into the bore 146 of the segment 154, FIG. 20, the balls are aligned with the groove 114 in the shank. The radially inwardly extending groove 114 permits the balls 150 to protrude radially inwardly at this location into the groove 114, engaging the handle to the shank. The spring 138 with manual release of sleeve 122, forces the sleeve 122 to the right in FIG. 20 forcing the balls 150 radially inwardly into the groove 114. In this position of the sleeve, the balls 150 are locked radially inwardly in the groove 114 by the sleeve 122. The balls can not move radially outwardly at this location due to the sleeve intermediate region 144 locking the balls radially inwardly in engagement with the groove 114. In this position, the sleeve and handle portion 80 are connected to the shank which can not rotate relative to the sleeve due to the pin 132.

To release the handle portion 80 from the shank, the sleeve is retracted until the step 142; is positioned as in FIG. 21. The shank at this position of the sleeve, can now be withdrawn to the right by displacing the balls 150 outwardly into the step 142 and out of the groove 114. The release position of the handle portion 80 is shown in FIG. 17 and the locked position is shown in FIG. 16.

The pin 96 projections from the chisel end 78, FIG. 12, limit the depth of penetration of the chisel into the vertebrae to form a partial channel in each vertebra.

In FIGS. 18 and 19 a box chisel 156 has a handle 158, a shank 160 and a chisel tip 162. In FIG. 19, the chisel tip 162 is rectangular in cross section and has a body 164 with an axial extending slot 166 for receiving bone chips during chiseling. The body has apertures 168 for s indicating depth of penetration into the vertebral disc space. The tip 162 has two blades 170 and 172 in parallel and lie in a plane that is normal to the longitudinal axis 174 of the shank 160. The tip 162 has holes 168 for indicating depth of penetration into the intervertebral disc space. The blades 170 and 172 have parallel first sides 174 and 176 and tapered second sides 178,180, respectively. The core 182 is hollow. A color coding ring 184 is attached to the handle to correspond the chisel to the same set as the other tools which are all color coded with the same color for a given set of tools for a given implant size. The two blades 170 and 172 engage the adjacent vertebrae previously engaged by the chisel 15 blades of the chisel 74 of FIGS. 11-13. The blades of the chisels 74 and 156 are arranged to form channels in the adjacent vertebrae of the same channel spacing across the disc space. The chisel 156 is dimensioned the same as the chisel 74 so as to lengthen the depth of channels formed by chisel 74 into the vertebrae.

The guide member 102 of the chisel 74 guides the chisel into the disc space so as to cut equal amounts of bone from the adjacent vertebrae and to center the chisel in the disc space between the adjacent vertebrae. The member guides the chisel 74 to form channels of partial depth into the vertebrae. This is referred to as a start chisel.

The chisel 156, FIGS. 18-19 is referred to as a finishing chisel as it finishes the channels in the vertebrae started by chisel 74. The channels formed by chisel 74 serve as a guide for the finishing chisel 156 so as to align the finishing chisel and form smooth complete fully formed channels in the adjacent vertebrae. No guide member is used on the chisel 156 as it is guided by the partially formed channels initially produced by the chisel 74. The blade spacing of the two chisels as well as their transverse blade widths are otherwise the same.

In practicing the posterior approach procedure with the aforementioned tools, the surgeon uses the posterior approach to reach the site in question and performs a discectomy. Sequentially sized distractors 35, FIG. 51 are then used to increasingly distract the vertebrae to the appropriate height h. The distractors 35 are first inserted with their flat wide surfaces 39 parallel to the vertebrae in a known manner. After insertion into the disc space the surgeon then rotates the distractor so that the flat blade end 38 is positioned between the adjacent vertebrae as shown in FIG. 51.

Optionally, the rotating scraper 60, FIGS. 5 and 6, are used to clean the disc material from the disc space and to prepare the vertebrae for the next step of forming the channels. Next, the chisel 74, FIGS. 11-13 and 15-17 is used to form a channel in each of the vertebrae. An appropriate size chisel is selected by the surgeon with a corresponding size distractor in place, the chisel is tapped into the contralateral side with the guide member 102 first inserted into the disc space D, FIG. 53. The guide member 102 has a height that is slightly smaller than the disc space D height h (FIG. 51). The chisels 74 are supplied in sets of differing dimensions to correspond to the other tools being used in the procedure and implant to be inserted. The implants are also supplied in sets of differing dimensions to accommodate differently dimensioned disc spaces D.

The guide member 102 helps ensure even endplate removal from both vertebrae. The guide pin 96 protruding from the chisel allows insertion of the chisel halfway into the vertebrae while preventing the extended guide from going too far into the space D. For example, if the vertebrae are distracted using a 7 mm distractor on one side, a 9 mm guided box chisel is used to create the bleeding bone necessary for fusion. The guide member has a height of about 7 mm or slightly less.

The guide member keeps the chisel centered in the disc space D with respect to the top and bottom vertebrae, so that the same amount of vertebral end plate is chiseled and removed on both the top and bottom surfaces of the vertebrae. The guided chisel 74 is impacted into one side of the disc space while the distractor is in place on the other side.

In a further example, if a 9 mm distractor is used, a 11 mm chisel is used on the contralateral side. The guide member 102 for this chisel has a height of about 9 mm or slightly less. In the alternative, with a 9 mm distractor in place on one side, a slightly smaller chisel can be used, for example, a 9 mm chisel with a guide member height of 7 mm. In any case, the chisel is impacted into the disc space until the pin 96 abuts the edge of the vertebral bodies. The pin 96 serves as visual and positive stop for the chisel. The chisel is then removed with a slap hammer as known in this art, which comprises a movable mass attached to a shaft which may be threaded to the handle of the chisel such as chisel 74. The handle has mating threads (not shown) for receiving the slap hammer. The channel is about 10 mm long in this example by chiseling up to the pin 96 stop. The pin 96 may be about 20 mm to the tip of the guide member 102.

At this time, the finishing chisel 156, FIGS. 18 and 19, is then inserted into the partially created channel, FIG. 54. This instrument is virtually identical in exterior dimensions to the box chisel 74 with the guide member 102 except the blades 92 and 94 of the chisel 74 are V-shaped and the blades of the chisel 156 are straight across normal to the longitudinal axis of the tool. The partial channel created by the chisel 74 serves as a guide for the chisel 156 to keep this chisel approximately centered within the disc space D relative to the height dimension h (FIG. 51). Chisel 156 is impacted until the desired depth is obtained. Typically this depth is 3 mm longer than the length of the implant being inserted.

The chisel 156 is then removed using a slap hammer attached to the chisel (not shown) in a manner described above for chisel 74. At this time a lordotic trial 40, FIG. 52, is inserted into the preformed channels to assess the fit of a proposed implant. If necessary, the chiseling may be repeated for the next larger size and the fit measured with an appropriately size trial. Once the trial has been used to assess the disc space D, to the surgeon's satisfaction, the implant is then inserted using an appropriate inserter tool.

The above steps are repeated on the opposite side of the disc space by removing the distractor 35, FIG. 51, at this side. The guided box starter chisel and finishing chisel may both be modular to accept the quick release handle 80, FIG. 15, and as described above in connection with the chisel 74, FIG. 16. The finishing chisel 156 not described as accepting the quick release handle in FIG. 18, but may also optionally be configured as the distal end of the chisel 74 to accept the quick release handle 80, FIG. 15. The quick connect handle 80 has a threaded bore in the end opposite the sleeve 122 for receiving a slap hammer (not shown). The guided and finishing box chisels as well as the other tools are color coded to indicate a set of tools that is dimensioned to be used together for a given implant size.

In FIGS. 24 and 25, chisel 186 is substantially the same as tool 74, FIGS. 11-13 except the guide member 188 may be a separate piece and fits within the cavity 190 inside the chisel tip 192. The member 188 is secured within the cavity by pin 194 which is press fit to the guide member 188 in one embodiment. In a further embodiment, the member 188 may be one piece with the tip 192. The pin 194 serves as a depth stop to limit the depth of insertion of the chisel into the disc space. In the various figures, protrusions similar to pin 194 serve primarily as a depth stop acting as a positive stop to limit the insertion depth of the chisels, as well as a visual depth limiting indicator. Such a pin or protrusion need only extend in one direction from the chisel tip. This chisel is used in the same manner as chisel 74 described above.

In FIG. 26, an alternate embodiment of a guided chisel 196 includes a retractable guide member 198. The chisel 196 includes a shank 200, a chisel tip 202 and a knurled handle 204. The tip 202 has two parallel blades 206, 208 and a hollow core 210, FIG. 27. The blades 206, 208 have straight edges normal to the longitudinal axis 212 and are formed as a conventional box chisel. The side walls 214 of the chisel terminate at the blade region at non-cutting edges and are recessed as shown from the plane of the edges of the blades. An axially extending slot 216 is formed in each of the side walls 214 and an axially extending slot 218 is formed in the top and bottom walls, 220, 222.

The tip 202 has a rectangular bore 224, FIGS. 27 and 28, which is in communication with the slots 216 and 218. The shank 200 and handle 204 have a circular cylindrical bore 225 in communication with bore 224 and the distal end of the handle 204 and extends through housing 228, FIG. 29. Housing 228 is attached to the distal end 226 of the handle 204, FIGS. 26 and 29. The housing 228 has a rectangular through opening 229 in communication with bore 225 which also passes through the housing 228. The housing is enlarged relative to the handle 204 and is rectangular in end view along the axis 212.

Guide member 198, FIGS. 31 and 32, is metal and rectangular in cross section and axially slides in the tip 202 bore 224 (FIGS. 32 and 33). The member 198 has a proximal end 230 that has chamfers 232 at the top and bottom surfaces. An axially extending through slot 234 is adjacent to the tip 230. A through bore 236 is in communication with the top and bottom surfaces of the member 198. A threaded axially extending blind bore 238 is in communication with the distal end of the member 198 opposite the end 230 and is aligned on axis 240, FIGS. 32 and 33. In FIG. 26, a pin 242 is press fit into bore 236, FIG. 32, of the guide member 198. The pin 242 passes through the slots 218 of the tip 202, FIG. 27, and is free to axially displace in these slots. The pin 242 passes through the slots 218 and protrudes above the top wall 220 and below the bottom wall 222 of the chisel tip 202 similar to pin 194 of chisel 186, FIG. 25. The pin 242 and member 198 are free to axially displace relative to the chisel blades 206, 208, FIG. 27. The top and bottom walls 220 and 222, respectively, have depth indicating indicia 244, FIG. 30, for indicating the depth of penetration of the chisel into the intervertebral disc space D.

In FIGS. 26 and 34, an elongated metal rod 246 has a threaded end portion 248 at the proximal end and a circular disc-like cap 250 at the distal end. Adjacent to the cap 250 the shaft of the rod has a square cross section 252.

In FIGS. 26, 36 and 37, a knob 254 which may be stainless steel or other materials, is a circular disc with finger gripping grooves 256 on its outer surface. A circular recess 258 is positioned at one external surface of the knob in communication with a square through bore 260. The recess 258 and bore 260 are in communication with opposite sides of the knob.

The knob is inserted first into the housing 228 opening 229, FIG. 26. The rod 246, FIG. 26, is then inserted into the bore 225 in the housing 228 through the recess 258 and bore 260 of the knob 254 and then into the bore 225 of the handle and shank, FIG. 29. The rod cap 250 sits in the recess 258. The rod square section 252 is located in the square bore 260 and is thus keyed to the knob by the section 252 and bore 260. The threaded end portion 248 of the rod is engaged with the threaded bore 238 of the guide member 198, FIG. 32. Rotation of the knob 254 rotates the rod 246. This rotation engages the threaded end portion of the rod to the threads of the guide member.

In operation, the rotation of the knob by the thumb of a user rotates the rod 246 relative to the guide member. This action displaces the guide member 198 to retract the guide member fully into the bore 224 of the chisel tip 202 or extend it fully. The retraction and extension is determined by the engagement of the pin 242, FIG. 26 with the slots 218 of the chisel tip 202. With the member 198 extended, the chisel is used as a starter chisel to commence chiseling the vertebrae similar in function to the chisel 74, FIG. 53. the pin 242, FIG. 26, serves to visually assist the surgeon to determine the depth of insertion of the chisel 196 as well as serve as a stop when the pin abuts the vertebrae as discussed above in connection with the use of chisel 74.

After the proper depth is achieved as determined by the pin 242, the knob 254, FIG. 26, is rotated to fully retract the guide member into the chisel tip 202 bore 224, FIG. 29. At this time the surgeon continues the chisel action as described above in connection with the finishing chisel 156, FIGS. 18, 19 and 54. In this case, the same chisel is used with and without a guide member to complete formation of the vertebrae channels. The steps for insertion of the implant are otherwise the same as described above.

FIGS. 38-50 show a second embodiment of a chisel 262 with a retractable guide member 264. In FIGS. 38, 41, 42 and 45, chisel 262 includes a rectangular in section chisel tip 266, a circular cylindrical in section shank 268 and a circular cylindrical handle section 270.

The tip 266 has two parallel blades 272, 274 and a hollow core 276, FIG. 46. The blades have straight edges normal to the longitudinal axis 278 and are formed as a conventional box chisel. The side walls 280 of the chisel terminate at the blade region at non-cutting edges 273 and are recessed as shown from the plane of the edges of the blades. An axially extending slot 282 is formed in each of the side walls 280 and an axially extending slot 284 is formed in the respective top and bottom walls, 286, 288.

The tip 266 has a rectangular bore 290, FIG. 46, which is in communication with the slots 282, 284 and core 276. The shank 268 and handle section 270 have a circular cylindrical bore 292 in communication with bore 290 and with the distal end of the handle section 270 and extends through reduced diameter cylindrical portion 294 of section 270, FIG. 42.

The reduced diameter portion, FIG. 43, has a pair of identical aligned elongated axially extending slots 296 on opposite sides thereof (only one slot being shown). The slots 296 each have a pair of detent grooves 298, one groove at each of opposite ends of each of the slots.

In FIGS. 41, 42, 49 and 50, a sleeve 300 slides over the reduced diameter portion 294 of the handle section 270 and is secured in place. The sleeve 300 has a pair of slots 302 aligned in opposing relation on opposite sides of the sleeve. The slots 302 are aligned with the slots 296 and grooves 298 of the reduced diameter portion 294 of the handle section 270 so that the slots 296 and grooves 298 are visible through the slots 302.

A rod 304, FIG. 41, has a collar 306 with a through bore 308. A pin 310 passes through the through bore 308 extending beyond the rod on each side. The pin 310 passes through the slots 302, FIG. 50, and 296, FIG. 43, in the respective sleeve 300 and handle portion 294. The rod 304 is inserted into the bores 290 and 292 of the shank 268 and tip 266. The proximal end 312 of the rod 304, FIG. 41, has a reduced diameter stud 314. The stud 314 is attached to guide member 264, FIG. 41, via a threaded bore (not shown) in the guide member 264. The guide member 264 is shaped similar to the guide member 198, FIG. 32 except that it has a relatively short threaded bore for receiving the stud 314 instead of the elongated threaded bore of the member 198, which receives the threaded end of the rod 246 of that embodiment. In FIG. 41, the rod stud 314 is attached to the guide member via the mating threads thereof. The rod 304 once attached to the guide member 264 does not rotate relative to the guide member.

Guide member 264, FIG. 41, is metal and rectangular in cross section and axially slides in the tip 266 core 276 and is substantially similar to the guide member of FIGS. 31 and 32. The member 264 has a proximal end that has chamfers at the top and bottom surfaces. An axially extending through slot is adjacent to the tip of the guide member. A through bore is in communication with the top and bottom surfaces of the member 264 for receiving the pin 314. A threaded axially extending blind bore is in communication with the distal end of the member 264 opposite the end 316 and is aligned on axis 318, FIG. 41. The pin 314 is press fit into bore of the guide member 264. The pin 314 passes through the slots 284 of the tip 266, FIG. 42, and is free to axially displace in these slots. The pin 314 passes through the slots 284 and protrudes above the top wall and below the bottom wall of the chisel tip 266 similar to pin 194 of chisel 186, FIG. 25. The top and bottom walls have depth indicating indicia for indicating the depth of penetration of the chisel into the intervertebral disc space D In operation, the pin 310, FIG. 38, is displaced in directions 312 to retract the guide member 264 fully into the core 276, FIGS. 46 and 47, or to fully extend the guide member as shown in FIGS. 38 and 48. The pin 310 in slots 296 and 302 (FIGS. 43 and 49) is displaced axially until aligned with either of the detent grooves 298, FIG. 43. At this time the pin 310 is rotated to seat the pin 310 in abutment with the surfaces forming the corresponding groove 298. This releasably locks the pin 310 in the axial position with the guide member 264 extended or retracted. The chisel in use is used similarly as the chisel of FIGS. 24-37 as described above. The chisel 262 of FIG. 38 is used in a two step procedure to first form a channel partially into the vertebrae with the guide member 264 extended until the pin 314 protruding from the tip 266, FIG. 41, abuts the adjacent vertebrae ends. This sets the depth of penetration as described previously. The guide member is then retracted and the channel is then finished to its desired depth.

In FIG. 45a, chisel 262' has V-shaped cutting blades 272' and 274' the same as that of chisel 74, FIG. 11. The rest of the chisel 262' is the same as the chisel 262, FIG. 45. Chisel 262' is arranged to have a retractable guide member (not shown in FIG. 45a) similar to that of chisel 262. Parts with the same reference numbers in FIG. 45 are the same. Parts with primed reference numerals in FIG. 45a are similar to the parts of FIG. 45 with the same reference numerals without the prime.

In FIG. 45b, chisel 262" have cutting blades 272" and 274" which are inclined relative to the longitudinal shank axis 271. The blade cutting edges lie in the plane of the top and bottom surfaces of the chisel tip 268" in this embodiment. They may be non-coplanar to the chisel end surfaces in other embodiments. The edges also lie in a second plane normal to the plane of the top and bottom surfaces. This latter second plane is inclined at an acute angle to the longitudinal axis 271 as shown in FIG. 45c. The rest of the chisel 262" is the same as the chisel 262, FIG. 45. Chisel 262" is arranged to have a retractable guide member similar to that of chisel 262, FIG. 45. In the alternative, this chisel may have a fixed guide member as shown for chisel 74, FIG. 11 or chisel 186, FIG. 24. Parts with the same reference numbers in FIG. 45 are the same. Parts with primed reference numerals (') in FIG. 45a are similar to the parts of FIG. 45 with the same reference numerals without the prime.

In the embodiments of FIGS. 11, 45a and 45b, the blade(s) terminates in a point in top plan view, the point either being formed by the blade as in FIG. 11 or by the blade at a side wall of the chisel tip portion such as at side wall 280" as in FIG. 45c. The angle of the blade edges to the longitudinal axis is set at a value that is determined to be optimal for the chiseling operation.

It will occur to one of ordinary skill that various modifications may be made to the disclosed embodiments. For example, chisels are described with a fixed guide member that is one piece or multiple pieces with the chisel tip and a retractable guide member. In addition, in further embodiments, the chisel blades have different configurations. In still further embodiments, the chisel has a an integral one piece handle or a releasable handle in addition to added structure for providing a retractable guide member. It should be understood that these embodiments of guide members, blade configurations and handle configurations may be employed in a given embodiment of a chisel in any combination of different configurations. It is intended that the scope of the invention is as defined in the appended claims.

The invention claimed is:

1. A chisel for preparing adjacent vertebrae for insertion of a spinal implant into the disc space defined by the vertebrae, the chisel comprising: a shank having a longitudinal axis and distal and proximal ends; and a bone cutting blade attached to the shank proximal end and having a cutting edge lying in a first plane for forming a channel in one of the vertebrae, the blade extending transverse to a second plane normal to the first plane, the second plane containing the longitudinal axis, wherein the cutting edge faces a proximal end of the chisel, wherein the cutting edge is non-linear in shape in a top plan view and has an apex in the top plan view, wherein the cutting edge has first and second cutting coplanar portions in the first plane, each first and second cutting coplanar portion tapering toward the proximal end of the chisel and wherein the proximal end of the shank has a hollow core facing the proximal end of the chisel, further including a chisel guide member movably attached to the shank for selectively extending from the core in a direction toward the proximal end of the chisel and retracting into the core in a direction toward a distal end of the chisel.

2. The chisel of claim 1 wherein the first and second cutting coplanar portions taper toward each other terminating at the apex.

3. The chisel of claim 1 wherein the first and second cutting coplanar portions are symmetrical relative to the longitudinal axis and the apex lies on the longitudinal axis.

4. The chisel of claim 1 wherein the bone cutting blade is a first bone cutting blade, and the chisel further comprises a second bone cutting blade configured substantially similarly to the first bone cutting blade, the second bone cutting blade being spaced apart from the first bond cutting blade such that each of the first and second bone cutting blades is positioned to remove bone from a different vertebra of the two adjacent vertebrae.

5. The chisel of claim 4 wherein the first and second bone cutting blades are symmetrical relative to each other.

6. The chisel of claim 1 wherein the shank has peripheral top and bottom surfaces, further including a projection extending at least from one of the top and bottom surfaces and spaced distally from the blade edge for abutting adjacent vertebrae during use of the chisel to limit the depth of penetration of the chisel into said vertebrae disc space.

7. The chisel of claim 6 wherein the projections each comprise a portion of a pin inserted in a through bore in the shank.

8. The chisel of claim 1 wherein the shank has a groove and a shoulder adjacent to the distal end thereof, further including a handle attached to the shank distal end and including a quick release sleeve arranged to be releasably secured to the groove and shoulder.

9. The chisel of claim 8 wherein the sleeve includes a pin for mating with the shoulder to preclude relative rotation of the sleeve and handle to the shank.

10. The chisel of claim 9 including a resilient member coupled to the sleeve for resiliently urging the sleeve to a quiescent second position to normally lock the handle to the shank in the quiescent second position.

11. The chisel of claim 10 wherein the shaft portion and the sleeve have juxtaposed spaced shoulders, the resilient member comprising a spring between and abutting said shoulders.

12. The chisel of claim 8 wherein the handle includes a shaft portion with a plurality of balls arranged in annular array about the shaft portion for radial displacement within corresponding bores, the sleeve having a stepped bore having first and second segments for receiving the shaft portion along said axis, the first segment for allowing the balls aligned therewith to be radially aligned with and external said groove in a first axial position of the sleeve to permit the shank to be disengaged from the shaft portion and the second segment for urging the balls into said groove in a second axial position to releasably lock the shaft portion to the shank.

13. The chisel of claim 1 wherein the bone cutting blade is a first bone cutting blade, and the chisel further comprises a second bone cutting blade configured substantially similarly to the first bone cutting blade, the first and second bone cutting blades in juxtaposed spaced relation, each of the first and second bone cutting blades for removing bone from a different one of the adjacent vertebrae.

14. The chisel of claim 1 wherein said guide member has a through slot, the shank including a pin fixed to the guide and movably attached to the shank in said slot so that the guide member can axially displace in said core in opposite directions along the longitudinal axis toward and away from the proximal end of the chisel.

15. The chisel of claim 14 wherein the pin protrudes from the shank to provide a visual indication of the depth of penetration of the chisel into the vertebral disc space and provides depth limiting means for abutting at least one of the vertebrae forming a stop for the chisel.

16. The chisel of claim 1 including guide member displacement means for selectively manually respectively extending and retracting the guide member out of and into the core.

17. The chisel of claim 16 wherein said displacement means comprises a first elongated member attached to the guide member and having a portion extending into the handle, and a rod displacement arrangement coupled to the elongated member portion for axially displacing the first rod toward and away from the proximal end of the chisel.

18. The chisel of claim 17 wherein the rod displacement means includes a transversely extending elongated member attached to the first rod at a first rod end and detent means attached to the handle for receiving the elongated member for selectively releasably securing the elongated member in guide member retracted and extended positions.

19. The chisel of claim 18 wherein the detent means comprises a slot in the handle for receiving the elongated member, the handle slot having first and second axially spaced channels each for selectively receiving the elongated member.

20. The chisel of claim 19 including a sleeve over the handle at the handle slot including a second slot juxtaposed with the handle slot.

21. The chisel of claim 17 wherein the rod is releasably attached to the guide member.

22. The chisel of claim 21 including threads for rotationally coupling the rod to the guide member, and a knob connected to the rod for rotating the rod relative to the guide member, the knob having a fixed axial position on the handle such that rotation of the knob displaces the guide member via the threaded engagement of the rod to the guide member.

23. The chisel of claim 22 wherein the knob is keyed to the rod to rotate the rod with rotation of the knob.

24. The chisel of claim 23 wherein the handle has a slot receiving the knob, the received knob for manual engagement by a thumb.

25. The chisel of claim 1 wherein the shank at the proximal end has at least one through slot for receiving bone chips during use of the chisel.

26. A chisel for preparing adjacent vertebrae for insertion of a spinal implant into the disc space defined by the vertebrae, the chisel comprising:
   a shank, the shank having a longitudinal axis, a core, and distal and proximal ends, the proximal end having top and bottom surfaces and opposing first and second side surfaces;
   first and second juxtaposed spaced bone cutting blades, each blade having a cutting edge lying in a first plane at the shank proximal end in a plane parallel to the respective top and bottom surfaces, each blade cutting edge facing in a proximal direction and extending transverse to the longitudinal axis in the first plane, a tangent to each blade cutting edge lying in a second plane normal to the first plane, the second plane being inclined relative to the longitudinal axis and relative to the opposing side surfaces in a direction toward the proximal end, the blade cutting edges each having a portion in which a tangent thereto intersects a side surface of the chisel in a top plan view at an acute angle;
   a guide member secured to the shank; and
   a pin passing through an axially extending slot in the shank and through the guide member for limiting the axial displacement of the guide member.

27. The chisel of claim 26 wherein the guide member is movably secured to the shank in the core and has a first retracted position located within the shank core and a second extended position extending beyond the shank at the proximal end for abutting adjacent vertebrae in the disc space during use.

28. The chisel of claim 27, including guide member displacement means for selectively manually respectively extending and retracting the guide member from and into the core.

29. The chisel of claim 27, further including a handle secured to the shank distal end and wherein said guide member displacement means comprises a first rod attached to the guide member and having a rod portion extending into the handle, and a rod displacement arrangement coupled to the rod portion for axially displacing the first rod toward and away from the proximal end.

30. The chisel of claim 29 further including a handle secured to the shank distal end wherein the rod displacement means includes a transversely extending second rod attached to the first rod at the first rod distal end.

31. The chisel of claim 30 including a detent means comprising a slot in the handle for receiving the second rod, the handle slot having first and second axially spaced channels each for selectively receiving the second rod.

32. The chisel of claim 31 including a sleeve positioned over the handle proximate the handle slot, wherein the sleeve includes a slot, and wherein the sleeve slot is aligned with the handle slot.

33. The chisel of claim 29 wherein the rod is releasably attached to the guide member.

34. The chisel of claim 33 including threads for rotationally coupling the rod to the guide member, and a knob connected to the rod for rotating the rod relative to the guide member, the knob having a fixed axial position on the handle such that rotation of the knob displaces the guide member via the threaded engagement of the rod to the guide member.

35. The chisel of claim 34 wherein the knob is keyed to the rod to rotate the rod with rotation of the knob.

36. The chisel of claim 35 wherein the handle has a slot receiving the knob, the received knob for manual engagement by a thumb.

37. The chisel of claim 26 wherein the pin protrudes from the shank to provide a visual indication of the depth of penetration of the chisel into the vertebral disc space and to provide depth limiting means for abutting at least one of the vertebrae forming a stop for the chisel during use.

38. The chisel of claim 26 wherein the shank at the proximal end has at least one through slot for receiving bone chips during use of the chisel.

39. A chisel for preparing adjacent vertebrae for insertion of a spinal implant into the disc space defined by the vertebrae, the chisel comprising: a shank having a longitudinal axis and distal and proximal ends; and a bone cutting blade attached to the shank proximal end and having a cutting edge lying in a first plane for forming a channel in one of the vertebrae, the blade extending transverse to a second plane normal to the first plane, the second plane containing the longitudinal axis, wherein the cutting edge faces a proximal end of the chisel, wherein the cutting edge is non-linear in shape in a top plan view and has an apex in the top plan view, wherein the cutting edge has first and second cutting coplanar portions in the first plane, each first and second cutting coplanar portion tapering toward the proximal end of the chisel, and wherein the shank has peripheral top and bottom surfaces, further including a projection extending at least from one of the top and bottom surfaces and spaced distally from the blade edge for abutting adjacent vertebrae during use of the chisel to limit the depth of penetration of the chisel into said vertebrae disc space.

40. A chisel for preparing adjacent vertebrae for insertion of a spinal implant into the disc space defined by the vertebrae, the chisel comprising: a shank having a longitudinal axis and distal and proximal ends; and a bone cutting blade attached to the shank proximal end and having a cutting edge lying in a first plane for forming a channel in one of the vertebrae, the blade extending transverse to a second plane normal to the first plane, the second plane containing the longitudinal axis, wherein the cutting edge faces a proximal end of the chisel, wherein the cutting edge is non-linear in shape in a top plan view and has an apex in the top plan view, wherein the cutting edge has first and second cutting coplanar portions in the first plane, each first and second cutting coplanar portion tapering toward the proximal end of the chisel, and wherein the shank has a groove and a shoulder adjacent to the distal end thereof, further including a handle attached to the shank distal end and including a quick release sleeve arranged to be releasably secured to the groove and shoulder.

41. A chisel for preparing adjacent vertebrae for insertion of a spinal implant into the disc space defined by the vertebrae, the chisel comprising:
   a shank, the shank having a longitudinal axis and having distal and proximal ends, the proximal end having top and bottom surfaces and opposing first and second side surfaces;
   first and second juxtaposed spaced bone cutting blades, each blade having a cutting edge lying in a first plane at the shank proximal end in a plane parallel to the respective top and bottom surfaces, each blade cutting edge facing a proximal end of the chisel and extending transverse to the longitudinal axis in the first plane, a tangent to the blade cutting edges lying in a second plane normal to the first plane, the second plane being inclined relative to the longitudinal axis and relative to the opposing side surfaces in a direction toward the proximal end of the chisel, the blade cutting edges each having a portion in which the tangent thereto intersects a side surface of the chisel in a top plan view at an acute angle;
   wherein the shank has a hollow core and includes a guide member movably secured to the shank in the core and having a first retracted position located within the shank core and a second extended position extending beyond the shank at the proximal end for abutting adjacent vertebrae in the disc space during use.

* * * * *